(12) United States Patent
Chen

(10) Patent No.: US 11,446,379 B2
(45) Date of Patent: Sep. 20, 2022

(54) MONOCLONAL ANTIBODIES THAT BIND TO SSEA4 AND USES THEREOF

(71) Applicant: CHO Pharma USA, Inc., Woburn, MA (US)

(72) Inventor: Lan Bo Chen, Lexington, MA (US)

(73) Assignee: CHO Pharma USA, Inc., Woburn, MA (US)

( * ) Notice: Subject to any disclaimer, the term of this patent is extended or adjusted under 35 U.S.C. 154(b) by 266 days.

(21) Appl. No.: 16/875,344

(22) Filed: May 15, 2020

(65) Prior Publication Data

US 2020/0276308 A1    Sep. 3, 2020

Related U.S. Application Data

(62) Division of application No. 15/940,334, filed on Mar. 29, 2018, now Pat. No. 10,688,182.

(51) Int. Cl.
| | | |
|---|---|---|
| *A61K 39/39* | (2006.01) | |
| *A61K 39/395* | (2006.01) | |
| *C07K 16/30* | (2006.01) | |
| *A61K 39/00* | (2006.01) | |
| *A61P 35/00* | (2006.01) | |

(52) U.S. Cl.
CPC ........ *A61K 39/39558* (2013.01); *C07K 16/30* (2013.01); *A61K 2039/505* (2013.01); *A61K 2039/51* (2013.01); *A61P 35/00* (2018.01); *C07K 2317/565* (2013.01)

(58) Field of Classification Search
None
See application file for complete search history.

(56) References Cited

U.S. PATENT DOCUMENTS

| | | |
|---|---|---|
| 2006/0019340 A1 | 1/2006 | Naor et al. |
| 2008/0299137 A1 | 12/2008 | Svedsen et al. |
| 2016/0102151 A1 | 4/2016 | Wong et al. |
| 2016/0347834 A1 | 12/2016 | Kato et al. |
| 2018/0030124 A1 | 2/2018 | Chen |

FOREIGN PATENT DOCUMENTS

| | | |
|---|---|---|
| JP | 2017/507118 A | 3/2017 |
| TW | 201620939 A | 6/2016 |
| WO | WO-2015/015489 A1 | 2/2015 |
| WO | WO-2015015489 A1 | 2/2015 |
| WO | WO-2018/039274 A1 | 3/2018 |
| WO | WO-2018039274 A1 | 3/2018 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*
Lin et al. "Improved Affinity of a Chicken Single-Chain Antibody to Avian Infectious Bronchitis Virus by Site-Directed Mutagenesis of Complementarity-Determining Region H3" African Journal of Biotechnology vol. 10, pp. 18294-18302, 2011.
Mariuzza et al. "The Structural Basis of Antigen-Antibody Recognition" Annual Review of Biophysics and Biophysical Chemistry vol. 16, pp. 139-159, 1987.
McCarthy et al. "Altering the Fine Specificity of an Anti-Legionella Single Chain Antibody by a Single Amino Acid Insertion" Journal of Immunological Methods vol. 251, pp. 137-149, 2001.
Sivasubramaniyan et al. "Expression of Stage-Specific Embryonic Antigen-4 (SSEA-4) Defines Spontaneous Loss of Epithelial Phenotype in Human Solid Tumor Cells" Glycobiology vol. 25, pp. 902-917, 2015.
Kavitha Sivasubramaniyan, et al. "Expression of stage-specific embryonic antigen-4 (SSEA-4) defines spontaneous loss of epithelial phenotype in human solid tumor cells." May 5, 2015. Glycobiology, 2015, vol. 25, No. 8. pp. 902-917.
Yi-Wei Lou, et al. "Stage-specific embryonic antigen-4 as a potential therapeutic target in glioblastoma multiforme and other cancers." PNAS. vol. 111, No. 7. pp. 2482-2487. Feb. 18, 2014.

* cited by examiner

*Primary Examiner* — Nelson B Moseley, II
(74) *Attorney, Agent, or Firm* — Cesari & McKenna, LLP

(57) ABSTRACT

A nucleic acid construct that encodes a monoclonal antibody or antigen-binding fragment that specifically binds to stage-specific embryonic antigen 4. The monoclonal antibody or antigen-binding fragment includes a heavy-chain CDR1 having the sequence of SEQ ID NO: 33 or SEQ ID NO: 40, a heavy-chain CDR2 having the sequence of SEQ ID NO: 34 or SEQ ID NO: 39, a heavy-chain CDR3 having the sequence of SEQ ID NO: 35 or SEQ ID NO: 41, a light-chain CDR1 having the sequence of SEQ ID NO: 36 or SEQ ID NO: 42, a light-chain CDR2 having the sequence of SEQ ID NO: 37 or SEQ ID NO: 43, and a light-chain CDR3 having the sequence of SEQ ID NO: 38 or SEQ ID NO: 44. Also disclosed are recombinant cells containing the nucleic acid construct.

14 Claims, 2 Drawing Sheets

Specification includes a Sequence Listing.

```
                                          HCDR1                           HCDR2
                      10        20        30        40        50        60
              ....|....|....|....|....|....|....|....|....|....|....|....|
huIGHV4-59x01 QVQLQESGPGLVKPSETLSLTCTVSGGSISSYYWSWIRQPPGKGLEWIGYIYYSGSTNYN
    huMAb1 H  ........................F.LT..GVD............V.WGG......
    huMab1 H1 ........................F.LT..GVD............V.WGG......
    huMab1 H2 ........................F.LT..GVD.V..........V.WGG......
    muMAb1 H  ....K.......A..QS..I....F.LT..GVD.V........L.V.WGG......

HCDR3
                      70        80        90        100       110
              ....|....|....|....|....|....|....|....|....|....|....
huIGHV4-59x01 PSLKSRVTISVDTSKNQFSLKLSSVTAADTAVYYCAR----------WGQGTLVTVSS
    huMAb1 H  SA.M..............................HEVLRGYALDY...........
    huMab1 H1 S..M.....K......V.................KHEVLRGYALDY...........
    huMab1 H2 SA.M..L...K.N...S.V...............KHEVLRGYALDY...........
    muMAb1 H  SA.M..LS..K.N...S.VF..MN.LQTD...M.KHEVLRGYALDY.....S......
```

Fig. 1A

```
                                          LCDR1                 LCDR2
                      10        20        30        40        50        60
              ....|....|....|....|....|....|....|....|....|....|....|....|
huIGκV3-11x01 EIVLTQSPATLSLSPGERATLSCRASQSVSSYLAWYQQKPGQAPRLLIYDASNRATGIPA
    huMAb1 L  ......................S..S...-.MH...............T.KL.S....
    huMab1 L1 .N....................S..S...-.MH...............T.KL.S....
    huMab1 L2 .N....................S..S...-.MH..........W....T.KL.S....
    muMAb1 L  .N......IM.A....KV.MT.S..S...-.MH.....SNTS.K.W...T.KL.S.V.G

LCDR3
                      70        80        90        100
              ....|....|....|....|....|....|....|....|....|..
huIGκV3-11x01 RFSGSGSGTDFTLTISSLEPEDFAVYYCQQRSNWP--FGQGTKVEIK
    huMAb1 L  ...........................F.G.GY.LT..........
    huMab1 L1 ........N.Y................F.G.GY.LT..........
    huMab1 L2 ....R...N.Y................F.G.GY.LT..........
    muMAb1 L  ....R...NSYS.....M.A..V.T..F.G.GY.LT..S...L...
```

Fig. 1B

```
                                    HCDR1                         HCDR2
                    10        20        30        40        50        60
               ....|....|....|....|....|....|....|....|....|....|....|....|
huIGHV4-59x01  QVQLQESGPGLVKPSETLSLTCTVS GGSISSYYWS WIRQPPGKGLEWIG YIYYSGSTNYN
    huMAb2 H   ........................ .F.LA..GVD .............. V.WGG......
   huMab2 H1   ........................ .F.LA..GVD .............. V.WGG......
   huMab2 H2   ........................ .F.LA..GVD .V............ V.WGG......
    muMAb2 H   ....K......A..QS..I..... .F.LA..GVD .V..........L. V.WGG......

HCDR3
                    70        80        90       100       110       120
               ....|....|....|....|....|....|....|....|....|....|....|....|
huIGHV4-59x01  PSLKS RVTISVDTSKNQFSLKLSSVTAADTAVYYCAR ----------- WGQGTLVTVSS
    huMAb2 H   SA.M. ............................... HGDSNSGYAMDY ...........
   huMab2 H1   S..M. .......K....L.................. KHGDSNSGYAMDY ...........
   huMab2 H2   SA.M. .L...K.N..S.L.................. KHGDSNSGYAMDY ...........
    muMAb2 H   SA.M. .L..NK.N..S.LF..MN.LQTD...M....K HGDSNSGYAMDY ....IS.....
```

Fig. 2A

```
                                        LCDR1                 LCDR2
                    10        20        30        40        50        60
               ....|....|....|....|....|....|....|....|....|....|....|....|
huIGκV3-11x01  EIVLTQSPATLSLSPGERATLSC RASQSVSSYLA WYQQKPGQAPRLLIY DASNRAT GIPA
    huMAb2 L   ...................... S..P...-.MH ............... .TYKL.S ....
   huMab2 L1   .N.................... S..P...-.MH ............... .TYKL.S ....
   huMab2 L2   .N.................... S..P...-.MH ..........W.... .TYKL.S ....
    muMAb2 L   .N.......IM.A....KV.MT. S..P...-.MH .....SSTS.K.W.. .TYKL.S V.G

LCDR3
                    70        80        90       100
               ....|....|....|....|....|....|....|....|....
huIGκV3-11x01  RFSGSGSGTDFTLTISSLEPEDFAVYYC QQRSNWP-- FGQGTKVEIK
    huMAb2 L   ............................ F.G.GF.LT ..........
   huMab2 L1   ........N.Y................. F.G.GF.LT ..........
   huMab2 L2   ........N.Y................. F.G.GF.LT ..........
    muMAb2 L   ........NSYS...RTM.A..V.T... F.G.GF.LT ..S...L...
```

Fig. 2B

MONOCLONAL ANTIBODIES THAT BIND TO SSEA4 AND USES THEREOF

CROSS-REFERENCE TO RELATED APPLICATIONS

This application is a divisional of U.S. application Ser. No. 15/940,334 filed on Mar. 29, 2018, now U.S. Pat. No. 10,688,182. The content of the prior application is hereby incorporated by reference in its entirety.

BACKGROUND

The goal of immunotherapy for cancer is to increase the strength of a patient's own immune responses against tumors. Immunotherapy can stimulate the activities of specific components of the immune system against cancer cells or can counteract signals produced by the cancer cells that suppress immune responses.

For example, antibodies have been developed as cancer vaccines which bind specifically to tumor-associated antigens (TAAs), e.g., protein antigens and carbohydrate antigens, on the surface of cancer cells, leading to antibody-dependent cellular cytotoxicity, antibody-dependent phagocytosis, and complement-dependent cell lysis, as well as direct cytostatic and/or cytotoxic effects.

Monoclonal antibody-based anti-cancer vaccines against several carbohydrate TAAs, e.g., Globo H, stage-specific embryonic antigen 3, and stage-specific embryonic antigen 4, have been developed. Yet, the need exists for improved monoclonal antibodies as anti-cancer vaccines having higher affinity for the carbohydrate TAA in order to promote more effective killing of cancer cells and to provide long-lasting resistance to cancer relapse.

SUMMARY

To meet the need set forth above, an isolated monoclonal antibody or antigen-binding fragment thereof is provided that specifically binds to stage-specific embryonic antigen 4 (SSEA4). The monoclonal antibody or antigen-binding fragment includes a heavy-chain CDR1 having the sequence of SEQ ID NO: 33 or SEQ ID NO: 40, a heavy-chain CDR2 having the sequence of SEQ ID NO: 34 or SEQ ID NO: 39, a heavy-chain CDR3 having the sequence of SEQ ID NO: 35 or SEQ ID NO: 41, a light-chain CDR1 having the sequence of SEQ ID NO: 36 or SEQ ID NO: 42, a light-chain CDR2 having the sequence of SEQ ID NO: 37 or SEQ ID NO: 43, and a light-chain CDR3 having the sequence of SEQ ID NO: 38 or SEQ ID NO: 44.

An isolated monoclonal antibody falling within the scope of the invention includes a heavy-chain sequence selected from SEQ ID NO: 2, SEQ ID NO:6, SEQ ID NO: 10, SEQ ID NO: 12, SEQ ID NO: 14, SEQ ID NO: 22, SEQ ID NO: 24, and SEQ ID NO: 26; and a light-chain sequence selected from SEQ ID NO: 4, SEQ ID NO: 8, SEQ ID NO: 16, SEQ ID NO: 18, SEQ ID NO: 20, SEQ ID NO: 28, SEQ ID NO: 30, and SEQ ID NO: 32.

Also provided is a method for treating a tumor in which cells in the tumor express SSEA4. The method is accomplished by administering an effective amount of the monoclonal antibody or antigen-binding fragment described above.

Further disclosed is a nucleic acid construct that encodes the above-described monoclonal antibody or antigen-binding fragment thereof, as well as a recombinant cell containing the nucleic acid construct. The recombinant cell expresses a monoclonal antibody or antigen-binding fragment thereof that specifically binds to SSEA4.

The details of several embodiments of the present invention are set forth in both the description and the drawings below. Other features, objects, and advantages of the invention will be apparent from the description and also from the appended claims. Finally, all references cited herein are hereby incorporated by reference in their entirety.

BRIEF DESCRIPTION OF THE DRAWINGS

The description below refers to the accompanying drawings, of which:

FIG. 1A is an amino acid alignment of germline human IGHV4-59×01 heavy-chain variable region (huIGHV4-59× 01: SEQ ID NO: 60) and corresponding amino acid sequences of anti-SSEA4 murine monoclonal antibody 1 (muMAb1 H; residues 20-138 of SEQ ID NO: 2) and human monoclonal antibody 1 sequences (huMAb1 H, residues 20-138 of SEQ ID NO: 10; huMAb1 H1, residues 20-138 of SEQ ID NO: 12; huMAb1 H2, residues 20-138 of SEQ ID NO: 14), the CDR regions being enclosed in boxes in this figure and all the other figures;

FIG. 1B is an amino acid alignment of germline human IGKV3-11×01 light-chain variable region (huIGKV3-11× 01; SEQ ID NO: 61) and corresponding amino acid sequences of anti-SSEA4 murine monoclonal antibody 1 (muMAb1 L; residues 23-128 of SEQ ID NO: 4) and human monoclonal antibody 1 sequences (huMAb1 L, residues 23-128 of SEQ ID NO: 16; huMAb1 L1, residues 23-128 of SEQ ID NO: 18; huMAb1 L2, residues 23-128 of SEQ ID NO: 20);

FIG. 2A is an amino acid alignment of germline human IGHV4-59×01 heavy-chain variable region (huIGHV4-59× 01: SEQ ID NO: 60) and corresponding amino acid sequences of anti-SSEA4 murine monoclonal antibody 2 (muMAb2 H; residues 20-139 of SEQ ID NO: 6) and human monoclonal antibody 2 sequences (huMAb2 H, residues 20-139 of SEQ ID NO: 22; huMAb2 H1, residues 20-139 of SEQ ID NO: 24; huMAb2 H2, residues 20-139 of SEQ ID NO: 26); and FIG. 2B is an amino acid alignment of germline human IGKV3-11×01 light-chain variable region and corresponding amino acid sequences of anti-SSEA4 murine monoclonal antibody 2 (muMAb2 L; residues 23-128 of SEQ ID NO: 8) and human monoclonal antibody 2 sequences (huMAb2 L, residues 23-128 of SEQ ID NO: 28; huMAb2 L1, residues 23-128 of SEQ ID NO: 30; huMAb2 L2, residues 23-128 of SEQ ID NO: 32).

DETAILED DESCRIPTION

As set forth, supra, a monoclonal antibody or antigen-binding fragment, e.g., single chain Fv, having the indicated CDR regions is provided that specifically binds to stage-specific embryonic antigen 4 (SSEA4). In an exemplary monoclonal antibody or antigen-binding fragment, the heavy-chain CDR1 (H-CDR1) has the sequence of SEQ ID NO: 33, the heavy-chain CDR2 (H-CDR2) has the sequence of SEQ ID NO: 34, the heavy-chain CDR3 (H-CDR3) has the sequence of SEQ ID NO: 35, the light-chain CDR1 (L-CDR1) has the sequence of SEQ ID NO: 42, the light-chain CDR2 (L-CDR2) has the sequence of SEQ ID NO: 43, and the light-chain CDR3 (L-CDR3) has the sequence of SEQ ID NO: 44.

Examples of monoclonal antibodies having the CDR regions identified in the preceding paragraph have the following combinations of heavy-chain sequence and light-chain sequence: (i) the heavy-chain sequence of SEQ ID NO: 14 and the light-chain sequence of SEQ ID NO: 28, (ii) the heavy-chain sequence of SEQ ID NO: 14 and the light-chain sequence of SEQ ID NO: 30, (iii) the heavy-chain sequence of SEQ ID NO: 14 and the light-chain sequence of SEQ ID NO: 32, (iv) the heavy-chain sequence of SEQ ID NO: 2 and the light-chain sequence of SEQ ID NO: 4, and (v) the heavy-chain sequence of SEQ ID NO: 6 and the light-chain sequence of SEQ ID NO: 8.

A nucleic acid construct encoding the monoclonal antibody or binding fragment includes sequences that encode the H-CDR1, H-CDR2, H-CDR3, L-CDR1, L-CDR2, and L-CDR3 regions listed above. In an example, the nucleic acid construct encodes the amino acids of SEQ ID NO: 33, SEQ ID NO: 34, SEQ ID NO: 35, SEQ ID NO: 42, SEQ ID NO: 43, and SEQ ID NO: 44.

In another aspect, the nucleic acid construct encodes a monoclonal antibody having the combinations of heavy-chain and light-chain sequences delineated above. Specific examples of such a nucleic acid construct each include one of the following combinations of sequences: (i) SEQ ID NO: 13 and SEQ ID NO: 27, (ii) SEQ ID NO: 13 and SEQ ID NO: 29, (iii) SEQ ID NO: 13 and SEQ ID NO: 31, (iv) SEQ ID NO: 1 and SEQ ID NO: 3, and (v) SEQ ID NO: 5 and SEQ ID NO: 7.

Moreover, a recombinant cell is provided that contains any of the just-mentioned nucleic acid constructs and expresses a monoclonal antibody or a binding fragment that specifically binds to SSEA4. A particular recombinant cell expresses a monoclonal antibody or binding fragment having the following CDR sequences: SEQ ID NO: 33, SEQ ID NO: 34, SEQ ID NO: 35, SEQ ID NO: 42, SEQ ID NO: 43, and SEQ ID NO: 44. An example of such a recombinant cell expresses a monoclonal antibody having the heavy-chain sequence of SEQ ID NO: 14 and the light-chain sequence of SEQ ID NO: 28.

The method mentioned above for treating a tumor can be carried out by administering any of the monoclonal antibodies disclosed in the application. In one example, the monoclonal antibody includes SEQ ID NO: 33, SEQ ID NO: 34, SEQ ID NO: 35, SEQ ID NO: 42, SEQ ID NO: 43, and SEQ ID NO: 44. The monoclonal antibody can have the heavy-chain sequence of SEQ ID NO: 14 and the light-chain sequence of SEQ ID NO: 28.

The tumor-treating method can be effective for treating breast, colon, gastrointestinal, kidney, lung, liver, ovarian, pancreatic, rectal, stomach, testicular, thymic, cervical, prostate, bladder, skin, nasopharyngeal, esophageal, oral, head and neck, bone, cartilage, muscle, lymph node, bone marrow, and brain cancer.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

EXAMPLES

Example 1: Hybridoma Production

Murine monoclonal antibodies against SSEA4 were produced using standard procedures. Briefly, mice were injected with SSEA4 fused to bovine serum albumin (BSA-SSEA4) together with an adjuvant once every two weeks for up to 10 weeks. Anti-SSEA4 antibody titers in blood samples were assayed by enzyme-linked immunosorbent assay (ELISA) using ELISA plates with bound BSA-SSEA4 under standard conditions.

Blood samples from mice having the highest titer by BSA-SSEA4 ELISA were also tested by ELISA using human pancreatic cancer (HPAC) cells that express SSEA4.

Splenocytes were isolated from the two mice having the highest antibody titers and fused with myeloma cells to form hybridomas using standard techniques. Hybridomas producing high titers of anti-SSEA4 antibodies were identified using standard subcloning procedures and ELISA assays with BSA-SSEA4 and HPAC cells. Hybridomas producing antibodies that bound to both HPAC and human melanoma cell line A375, which does not express SSEA4, were not pursued further.

Antibodies binding to cell surface SSEA4 were validated using a fluorescence-activated cell sorting assay by incubating HPAC cells and A375 cells with hybridoma supernatants, followed by incubation with a fluorescently labelled secondary antibody. Two monoclonal antibodies, designated as murine monoclonal antibody 1 (muMAb1) and murine monoclonal antibody 2 (muMAb2), were selected for further analysis. Both of these monoclonal antibodies bind to BSA-SSEA4 and HPAC cells and do not bind to A375 cells.

Isotype analysis indicated that muMAb1 is an IgG1 kappa antibody and muMAb2 is an IgG3 kappa antibody.

Monoclonal antibody concentrations in hybridoma supernatants and binding affinity for SSEA4 were determined as described in the following two sections. The $K_d$ value for muMAb1 was 0.22 nM and the $K_d$ value for muMAb2 was 0.08 nM.

Example 2: Determination of Antibody Concentration by ELISA

The concentrations of muMAb antibodies in media samples were determined by ELISA with the following primary antibodies coated on ELISA plates. For murine MAbs, ELISA plates were coated with AffiniPure Goat Anti-Mouse IgG (H+L) (Jackson ImmunoResearch #115-005-062) at 1 µg/ml, 100 µl/well overnight. After incubation with serial dilution of hybridoma supernatants or media samples from transient transfections (see below), wells were washed thoroughly and bound antibodies detected by adding Peroxidase AffiniPure Goat Anti-Mouse IgG (H+L) (Jackson ImmunoResearch #115-035-062) at a 1:8,000 dilution. After thorough washing, ABTS Peroxidase Substrate (1 Component) (KPL #50-66-06) was added and absorbance of each well at 405 nm was measured.

For humanized mAbs (see below), ELISA plates were coated with AffiniPure F(ab')₂ Fragment Goat Anti-Human IgG, Fcγ Fragment Specific (Jackson ImmunoResearch #109-006-098) 1 µg/ml, 100 µl/well, overnight. Detection of bound humanized antibodies was performed using Peroxidase AffiniPure Goat Anti-Human IgG, Fcγ fragment specific (Jackson ImmunoResearch #109-035-008) at a 1:10,000 dilution as described above for murine antibodies.

Example 3: Determination of Antibody Affinities by ELISA

Standard ELISA procedures were performed for the determination of antigen binding affinity using the following sets of reagents. ELISA plates were coated with BSA-SSEA4 at a 1:1000 dilution. Samples of serially-diluted hybridoma supernatants or transient transfection samples were added to each well, followed by thorough washing. The following secondary antibodies were used to detect muMAbs and huMAbs bound to the antigen on the plate: For muMAb1, AffiniPure Goat Anti-Mouse IgG, Fcγ Subclass 1 Specific (Jackson ImmunoResearch #115-005-205) at a 1:2,500 dilution, for muMAb2, AffiniPure Goat Anti-Mouse IgG, Fcγ Subclass 3 Specific (Jackson ImmunoResearch #115-005-209) at a 1:2,500 dilution, for all humanized antibodies, AffiniPure Goat Anti-Human IgG (H+L) (Jackson ImmunoResearch #109-005-088) at a 1:2,500 dilution.

Plate-bound secondary antibodies were detected using Peroxidase AffiniPure Bovine Anti-Goat IgG (H+L) (Jackson ImmunoResearch #805-035-180) at a 1:6,000 dilution and developed as set forth above.

Example 4: Cloning of Antibody Genes

VH and VL antibody sequences were cloned from hybridomas as follows. Total RNA was isolated from approximately 5-7×10⁶ hybridoma cells using TRIZOL reagent (Invitrogen, cat #15596-026) as directed by the manufacturer. First strand cDNA synthesis was carried out using Maxima Universal First Strand cDNA synthesis kit (Thermo Fisher cat. #K1661) with 6 μg total RNA and the following gene specific primers: murine IgG1 VH: TATGCAAGGCTTACAACCACA (SEQ ID NO: 45), murine IgG3 VH: GGGGGTACTGGGCTTGGGTAT (SEQ ID NO: 46), and murine kappa VL: CTCATTCCTGTTGAAGCTCTTGAC (SEQ ID NO: 47).

Following first strand cDNA synthesis, a poly A sequence was appended to the 5' end of each first strand cDNA with terminal transferase. The resultant 5' end tailed cDNA products were subjected to two rounds of PCR amplification. The first round PCR reaction was carried out with Herculase II DNA polymerase (Agilent Technologies cat #600679) with the following primers: 5' GTGACTCGAGTCGACATCGA TTTTTTTTTTTTTTTT (SEQ ID NO: 48), 3' primer for murine IgG1 VH: CTTCCGGAATTCCTCAATTTTCTTGTCCACCTTGGTGC (SEQ ID NO: 49), 3' primer for murine IgG3 VH: CTTCCGGAATTCCTCGATTCTCTTGATCA ACTCAGTCT (SEQ ID NO: 50), and 3' primer for murine kappa VL: CTTCCGGAATTCCTCATTCCTGTTGAAGCTCTTGACAATGGG (SEQ ID NO: 51).

A fraction (1/20) of the first round PCR products was further amplified in a second round of PCR using Phusion High Fidelity DNA polymerase (Fisher Scientific cat #F530L) with the following primers: 5' GTGACTCGAGTCGACATCGATTT TTTTTTTTTTTTT (SEQ ID NO: 48), 3' primer for murine IgG1 VH: ATTAAGTCGACATAGACAGATGGGGGTGTCGTTTTGGC (SEQ ID NO: 52), 3' primer for murine IgG3 VH: ATTAAGTCGACAGGGACCAAGGGATAG ACAGATGG (SEQ ID NO: 53), and 3'primer for murine kappa VL: CTACCTCGAGGGATACAGTTGGTGCAGCATC (SEQ ID NO: 54).

The resulting PCR products were digested with pairs of restriction enzymes, ClaI/SalI for the VH PCR fragments and ClaI/XhoI for the VL PCR fragments and inserted into a cloning vector using standard recombinant DNA procedures. Clones containing inserts in the appropriate size range were sequenced in order to identify full length VH/VL clones.

Example 5: Construction of Full-Length Murine Antibody Expression Vectors

Full-length murine IgG heavy and light chain expression plasmids were constructed as follows.

First strand cDNA synthesis was carried out by reverse transcriptase (RT) using Maxima Universal First Strand cDNA synthesis kit (Thermo Fisher cat #K1661) with 6 μg total RNA from hybridomas identified above as containing full-length VH and VL sequences. An oligo dT primer and random hexamer primers were employed in separate RT reactions. The oligo dT and random primed RT products were combined and used as the source of full length cDNA for muMAb1 and muMAb2, via a round of PCR amplification using Phusion High Fidelity DNA polymerase (Fisher Scientific cat #F530L) with the following set of primers, which were designed using the sequence information obtained above. For muMAb1 and muMAb2 kappa light chain 5'primer CAGTCCGCGGCCACCATGGATTTTCAAGTGCAGATTTTC (SEQ ID NO: 55), 3' primer AGGAAGATCTAACACTCATTCCTGTTGAAGC (SEQ ID NO: 56). For muMAb1 murine IgG1 heavy chain 5' CAGTCCGCGGCCACCATGGCTGTC CTGGTGCTGTT (SEQ ID NO: 57), 3' primer CTGGACAGGGATCCAGAGTTCCA (SEQ ID NO: 58). For muMAb2 murine IgG3 heavy chain 5' primer CAGTCCGCGG CCACCATGGCTGTCCTGGTGCTGTT (SEQ ID NO: 57), 3' primer CATGAGA TCTCATTTACCAGGGGAGCGAGA (SEQ ID NO: 59).

The amplified muMAb1 and muMAb2 murine kappa light chain sequences and the muMAb2 murine IgG3 heavy chain sequence were directly cloned into a mammalian expression plasmid as SacII/BglII restriction fragments. The muMAb1 murine IgG1 heavy chain amplification product represents the 5' end of the gene coding sequences, just past an internal BamHI site that corresponds to approximately the midpoint of the CH1 region. It was cloned into a previously constructed full-length mouse IgG1 heavy chain expression plasmid as a SacII/BamHI restriction fragment. All clones were verified by sequencing.

The SEQ ID NOs corresponding to the amino acid sequences of muMAb1 and muMAb2 are shown below in Table 1.

TABLE 1

Full-length heavy and light chain monoclonal antibody sequences

| mAb | Heavy chain | mAb | Light chain |
|---|---|---|---|
| muMAb1 H | SEQ ID NO: 2 | muMAb1 L | SEQ ID NO: 4 |
| muMAb2 H | SEQ ID NO: 6 | muMAb2 L | SEQ ID NO: 8 |
| huMAb1 H | SEQ ID NO: 10 | huMAb1 L | SEQ ID NO: 16 |
| huMAb1 H1 | SEQ ID NO: 12 | huMAb1 L1 | SEQ ID NO: 18 |
| huMAb1 H2 | SEQ ID NO: 14 | huMAb1 L2 | SEQ ID NO: 20 |
| huMAb2 H | SEQ ID NO: 22 | huMAb2 L | SEQ ID NO: 28 |
| huMAb2 H1 | SEQ ID NO: 24 | huMAb2 L1 | SEQ ID NO: 30 |
| huMAb2 H2 | SEQ ID NO: 26 | huMAb2 L2 | SEQ ID NO: 32 |

Example 6: Humanization

In order to humanize muMAb1 and muMAb2, human immunoglobulin germline sequences having the highest degree of homology to the murine antibody sequences were identified by comparison of the murine sequences to a human immunoglobulin gene database. The results indicated that the closest human germline sequences to the heavy chain of both muMAb1 and muMAb2 was huIGHV4-59×01, and the closest light chain to both muMAb1 and muMAb2 was huIGKV3-11×01.

For humanization of muMAb1 and muMAb2, CDR regions were grafted onto human sequences to create huMAb1 and huMAb2, respectively. The SEQ ID NOs corresponding to the amino acid sequences of huMAb1 and huMAb2 heavy and light chains are shown above in Table 1.

Mutations in the huMAb1 and huMAb2 sequences were designed in silico to maximize degree of humanization and to provide structural support for CDR loops. The amino acid changes and their positions in the heavy and light chain sequences are shown in Tables 2-5 below, as well as in FIGS. 1A, 1B, 2A, and 2B.

TABLE 2

Mutations in huMAb1 heavy chain sequences

| residue | H1 | H2 |
| --- | --- | --- |
| Ile 37 |  | Val |
| Ala 62 | Ser |  |
| Val 67 |  | Leu |
| Val 71 | Lys | Lys |
| Thr 73 |  | Asn |
| Asn 76 |  | Ser |
| Phe 78 | Val | Val |
| Arg 97 | Lys | Lys |

TABLE 3

Mutations in huMAb1 light chain sequences

| residue | L1 | L2 |
| --- | --- | --- |
| Ile 2 | Asn | Asn |
| Leu 47 |  | Trp |
| Ser 65 |  | Arg |
| Thr 69 |  | Asn |
| Phe 71 | Tyr | Tyr |

TABLE 4

Mutations in huMAb2 heavy chain sequences

| residue | H1 | H2 |
| --- | --- | --- |
| Ile 37 |  | Val |
| Ala 62 | Ser |  |
| Val 67 |  | Leu |
| Val 71 | Lys | Lys |
| Thr 73 |  | Asn |
| Asn 76 |  | Ser |
| Phe 78 | Val | Val |
| Arg 97 | Lys | Lys |

TABLE 5

Mutations in huMAb2 light chain sequences

| Residue | L1 | L2 |
| --- | --- | --- |
| Ile 2 | Asn | Asn |
| Leu 47 |  | Trp |
| Thr 69 | Asn | Asn |
| Phe 71 | Tyr | Tyr |

The SEQ ID NOs. corresponding to the amino acid sequences encoded by the mutated full-length heavy and light chain genes are shown above in Table 1.

The SEQ ID NOs of all CDR sequences of the above antibodies are shown below in Table 6.

TABLE 6

SEQ ID NOs corresponding to CDR regions

| CDR | muMAb1/hMAb1 | muMAb2/hMAb2 |
| --- | --- | --- |
| HCDR1 | SEQ ID NO: 33 | SEQ ID NO: 40 |
| HCDR2 | SEQ ID NO: 34 | SEQ ID NO: 34 |
| HCDR3 | SEQ ID NO: 35 | SEQ ID NO: 41 |
| HCDR2 H1[a] | SEQ ID NO: 39 | SEQ ID NO: 39 |
| LCDR1 | SEQ ID NO: 36 | SEQ ID NO: 42 |
| LCDR2 | SEQ ID NO: 37 | SEQ ID NO: 43 |
| LCDR3 | SEQ ID NO: 38 | SEQ ID NO: 44 |

[a]huMAb1 H1 and huMAb2 H1 both include a forward mutation in HCDR2

Example 7: Construction of Humanized Antibody Expression Vectors

Construction of full length humanized heavy and light chain expression plasmids was done using standard recombinant DNA techniques. Fragments were cloned as appropriate into (i) a construct containing full length human IgG1 heavy chain with silent mutations introduced to generate an NheI restriction site at the beginning of the CH1 region, and (ii) a full length human kappa light chain with silent mutations introduced to generate a BsiWI restriction site at the beginning of the CL constant region.

DNA fragments having sequences based on the mutated variants discussed above were synthesized and cloned into the appropriate expression vectors using standard techniques.

Example 8: Production of Recombinant Antibodies Via Transient Transfection in 293T Cells The human 293T embryonic kidney epithelial cell line was maintained in DMEM (HyClone cat #SH30243.02) supplemented with 10% heat-inactivated fetal bovine serum, 2 mM L-glutamine, and penicillin/streptomycin; (GIBCO cat #15140). Expression constructs were introduced into the cells via poly(ethylenimine) (PEI) mediated transfection. Briefly a DNA mix was prepared by combining heavy and light chain expression plasmids in a 1:1 ratio. PEI/DNA complexes were then formed at a 1.5:1 PEI to DNA ratio, and, after incubation for 20 minutes, added to the cultured cells. Two days after transfection, the culture media were removed and replaced with fresh media. Supernatants were harvested for analysis at day five following the transfection.

Large-scale production of recombinant antibodies was performed by transfecting the heavy and light chain expression plasmids into human 293T cells as described above. After three days, the transfected cells were harvested and seeded into serum free media (HyClone CDM4HEK293 cat #SH3085802) supplemented with 6 mM L-glutamine in shaker flasks. Cell growth and antibody production was monitored and the culture supernatants were harvested for antibody purification when the cell viability fell below 50%.

Expression of different combinations of heavy chains and light chains were performed by co-transfection of heavy and light chain expression plasmids as described above. Affinities of these recombinant antibodies are shown in Table 7 below.

TABLE 7

Summary of binding affinities of recombinant antibodies

| Anti-SSEA4 Ab | Heavy chain | Light chain | $K_d$ (nM) | Index[a] |
|---|---|---|---|---|
| muMAb1 | muMAb1 H | muMAb1 L | 0.17 | 0.9 |
| muMAb2 | muMAb2 H | muMAb2 L | 0.19 | 1.1 |
| huMAb1 | huMAb1 H | huMAb1 L | N.D.[b] | —[c] |
| huMAb1a | huMAb1 H2 | huMAb1 L1 | 4.3 | 23.9 |
| huMAb1b | huMAb1 H2 | huMAb1 L2 | 4.7 | 26.1 |
| huMAb2 | huMAb2 H | huMAb2 L | N.D.[b] | —[c] |
| huMAb2a | huMAb2 H2 | huMAb2 L2 | 5.7 | 31.7 |
| huMAb3 | huMAb1 H2 | huMAb2 L | 0.09 | 0.5 |
| huMAb4 | huMAb1 H2 | huMAb2 L1 | 0.10 | 0.6 |
| huMAb5 | huMAb1 H2 | huMAb2 L2 | 0.14 | 0.8 |

[a]Index was obtained by normalizing the $K_d$ with the average $K_d$ of muMAb1 and muMAb2 (0.18).
[b]Binding not detected
[c]Not determined Biding affinities of two recombinant humanized antibodies, namely, huMAb3 and huMAb4 were also determined by a surface plasmon resonance assay using standard procedures. The $K_d$ value of huMAb3 was between 50 nM and 90 nM. The $K_d$ value of huMAb4 was approximately 0.4 μM.

The results showed that huMAb3 had a high affinity for SSEA4 as measured by either ELISA or by surface plasmon resonance.

Other Embodiments

All of the features disclosed in this specification may be combined in any combination. Each feature disclosed in this specification may be replaced by an alternative feature serving the same, equivalent, or similar purpose. Unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

---

What is claimed is:

1. A nucleic acid construct that encodes a monoclonal antibody, the construct encoding a heavy-chain CDR1 (H-CDR1) having the sequence of SEQ ID NO: 33, a heavy-chain CDR2 (H-CDR2) having the sequence of SEQ ID NO: 34, a heavy-chain CDR3 (H-CDR3) having the sequence of SEQ ID NO: 35, a light-chain CDR1 (L-CDR1) having the sequence of SEQ ID NO: 42, a light-chain CDR2 (L-CDR2) having the sequence of SEQ ID NO: 43, and a light-chain CDR3 (L-CDR3) having the sequence of SEQ ID NO: 44,
   wherein the monoclonal antibody specifically binds to stage-specific embryonic antigen 4.

2. A nucleic acid construct that encodes a monoclonal antibody having a heavy-chain sequence of SEQ ID NO: 2and SEQ ID NO: 26; and a light-chain sequence of SEQ ID NO: 4; a heavy-chain sequence of SEQ ID NO: 6 and a light-chain sequence of SEQ ID NO: 8; or a heavy-chain sequence of SEQ ID NO: 14 and a light-chain sequence of SEQ ID NO: 28, SEQ ID NO: 30, or SEQ ID NO: 32, wherein the monoclonal antibody specifically binds to stage-specific embryonic antigen 4.

3. The nucleic acid construct of claim 2, wherein the heavy-chain sequence is SEQ ID NO: 14 and the light-chain sequence is SEQ ID NO: 28.

4. The nucleic acid construct of claim 2, wherein the heavy-chain sequence is SEQ ID NO: 14 and the light-chain sequence is SEQ ID NO: 30.

5. The nucleic acid construct of claim 2, wherein the heavy-chain sequence is SEQ ID NO: 14 and the light-chain sequence is SEQ ID NO: 32.

6. The nucleic acid construct of claim 2, wherein the heavy-chain sequence is SEQ ID NO: 2 and the light-chain sequence is SEQ ID NO: 4.

7. The nucleic acid construct of claim 2, wherein the heavy-chain sequence is SEQ ID NO: 6 and the light-chain sequence is SEQ ID NO: 8.

8. A recombinant cell comprising the nucleic acid construct of claim 1, wherein the cell expresses a monoclonal antibody that specifically binds to stage-specific embryonic antigen 4.

9. A recombinant cell comprising the nucleic acid construct of claim 2, wherein the cell expresses a monoclonal antibody that specifically binds to stage-specific embryonic antigen 4.

10. The recombinant cell of claim 9, wherein the heavy-chain sequence is SEQ ID NO: 14 and the light-chain sequence is SEQ ID NO: 28.

11. The recombinant cell of claim 9, wherein the heavy-chain sequence is SEQ ID NO: 14 and the light-chain sequence is SEQ ID NO: 30.

12. The recombinant cell of claim 9, wherein the heavy-chain sequence is SEQ ID NO: 14 and the light-chain sequence is SEQ ID NO: 32.

13. The recombinant cell of claim 9, wherein the heavy-chain sequence is SEQ ID NO: 2 and the light-chain sequence is SEQ ID NO: 4.

14. The recombinant cell of claim 9, wherein the heavy-chain sequence is SEQ ID NO: 6 and the light-chain sequence is SEQ ID NO: 8.

* * * * *

SEQUENCE LISTING

<160> NUMBER OF SEQ ID NOS: 61

<210> SEQ ID NO 1
<211> LENGTH: 1389
<212> TYPE: DNA
<213> ORGANISM: Mus musculus
<220> FEATURE:
<221> NAME/KEY: CDS
<222> LOCATION: (1)..(1389)
<223> OTHER INFORMATION: heavy chain

<400> SEQUENCE: 1

```
atg gct gtc ctg gtg ctg ttc ctc tgc ctg gtt gca ttt cca agc tgt      48
Met Ala Val Leu Val Leu Phe Leu Cys Leu Val Ala Phe Pro Ser Cys
1               5                   10                  15 gtc ctg tcc cag gtg cag ctg aag gag tca gga cct ggc ctg gtg gcg      96
Val Leu Ser Gln Val Gln Leu Lys Glu Ser Gly Pro Gly Leu Val Ala
            20                  25                  30 ccc tca cag agc ctg tcc atc act tgc act gtc tct ggg ttt tca tta     144
Pro Ser Gln Ser Leu Ser Ile Thr Cys Thr Val Ser Gly Phe Ser Leu
        35                  40                  45 acc agc tat ggt gta gac tgg gtt cgc cag cct cca gga aag ggt ctg     192
Thr Ser Tyr Gly Val Asp Trp Val Arg Gln Pro Pro Gly Lys Gly Leu
    50                  55                  60 gag tgg ctg gga gta ata tgg ggt ggt gga agc aca aat tat aat tca     240
Glu Trp Leu Gly Val Ile Trp Gly Gly Gly Ser Thr Asn Tyr Asn Ser
65                  70                  75                  80 gct ctc atg tcc aga ctg agc atc agc aaa gac aac tcc aag agc caa     288
Ala Leu Met Ser Arg Leu Ser Ile Ser Lys Asp Asn Ser Lys Ser Gln
                85                  90                  95 gtt ttc tta aaa atg aac agt ctg caa act gat gac aca gcc atg tac     336
Val Phe Leu Lys Met Asn Ser Leu Gln Thr Asp Asp Thr Ala Met Tyr
            100                 105                 110 tac tgt gcc aaa cat gag gta cta cgg ggg tat gct ctg gac tac tgg     384
Tyr Cys Ala Lys His Glu Val Leu Arg Gly Tyr Ala Leu Asp Tyr Trp
        115                 120                 125 ggt caa gga acc tca gtc acc gtc tcc tca gcc aaa acg aca ccc cca     432
Gly Gln Gly Thr Ser Val Thr Val Ser Ser Ala Lys Thr Thr Pro Pro
    130                 135                 140
```

|  |  |
|---|---|
| tct gtc tat cca ctg gcc cct gga tct gct gcc caa act aac tcc atg<br>Ser Val Tyr Pro Leu Ala Pro Gly Ser Ala Ala Gln Thr Asn Ser Met<br>145                            150                        155                        160 | 480 |
| gtg acc ctg gga tgc ctg gtc aag ggc tat ttc cct gag cca gtg aca<br>Val Thr Leu Gly Cys Leu Val Lys Gly Tyr Phe Pro Glu Pro Val Thr<br>                     165                        170                        175 | 528 |
| gtg acc tgg aac tct gga tcc ctg tcc agc ggt gtg cac acc ttc cca<br>Val Thr Trp Asn Ser Gly Ser Leu Ser Ser Gly Val His Thr Phe Pro<br>                180                        185                        190 | 576 |
| gct gtc ctg cag tct gac ctc tac act ctg agc agc tca gtg act gtc<br>Ala Val Leu Gln Ser Asp Leu Tyr Thr Leu Ser Ser Ser Val Thr Val<br>              195                        200                       205 | 624 |
| ccc tcc agc acc tgg ccc agc gag acc gtc acc tgc aac gtt gcc cac<br>Pro Ser Ser Thr Trp Pro Ser Glu Thr Val Thr Cys Asn Val Ala His<br>210                          215                        220 | 672 |
| ccg gcc agc agc acc aag gtg gac aag aaa att gtg ccc agg gat tgt<br>Pro Ala Ser Ser Thr Lys Val Asp Lys Lys Ile Val Pro Arg Asp Cys<br>225                          230                        235                        240 | 720 |
| ggt tgt aag cct tgc ata tgt aca gtc cca gaa gta tca tct gtc ttc<br>Gly Cys Lys Pro Cys Ile Cys Thr Val Pro Glu Val Ser Ser Val Phe<br>                     245                        250                        255 | 768 |
| atc ttc ccc cca aag ccc aag gat gtg ctc acc att act ctg act cct<br>Ile Phe Pro Pro Lys Pro Lys Asp Val Leu Thr Ile Thr Leu Thr Pro<br>                260                        265                        270 | 816 |
| aag gtc acg tgt gtt gtg gta gac atc agc aag gat gat ccc gag gtc<br>Lys Val Thr Cys Val Val Val Asp Ile Ser Lys Asp Asp Pro Glu Val<br>              275                        280                        285 | 864 |
| cag ttc agc tgg ttt gta gat gat gtg gag gtg cac aca gct cag acg<br>Gln Phe Ser Trp Phe Val Asp Asp Val Glu Val His Thr Ala Gln Thr<br>            290                        295                        300 | 912 |
| caa ccc cgg gag gag cag ttc aac agc act ttc cgc tca gtc agt gaa<br>Gln Pro Arg Glu Glu Gln Phe Asn Ser Thr Phe Arg Ser Val Ser Glu<br>305                          310                        315                        320 | 960 |
| ctt ccc atc atg cac cag gac tgg ctc aat ggc aag gag ttc aaa tgc<br>Leu Pro Ile Met His Gln Asp Trp Leu Asn Gly Lys Glu Phe Lys Cys<br>                     325                        330                        335 | 1008 |
| agg gtc aac agt gca gct ttc cct gcc ccc atc gag aaa acc atc tcc<br>Arg Val Asn Ser Ala Ala Phe Pro Ala Pro Ile Glu Lys Thr Ile Ser<br>                  340                        345                        350 | 1056 |
| aaa acc aaa ggc aga ccg aag gct cca cag gtg tac acc att cca cct<br>Lys Thr Lys Gly Arg Pro Lys Ala Pro Gln Val Tyr Thr Ile Pro Pro<br>                     355                        360                        365 | 1104 |
| ccc aag gag cag atg gcc aag gat aaa gtc agt ctg acc tgc atg ata<br>Pro Lys Glu Gln Met Ala Lys Asp Lys Val Ser Leu Thr Cys Met Ile<br>              370                        375                        380 | 1152 |
| aca gac ttc ttc cct gaa gac att act gtg gag tgg cag tgg aat ggg<br>Thr Asp Phe Phe Pro Glu Asp Ile Thr Val Glu Trp Gln Trp Asn Gly<br>385                          390                        395                        400 | 1200 |
| cag cca gcg gag aac tac aag aac act cag ccc atc atg gac aca gat<br>Gln Pro Ala Glu Asn Tyr Lys Asn Thr Gln Pro Ile Met Asp Thr Asp<br>                     405                        410                        415 | 1248 |
| ggc tct tac ttc gtc tac agc aag ctc aat gtg cag aag agc aac tgg<br>Gly Ser Tyr Phe Val Tyr Ser Lys Leu Asn Val Gln Lys Ser Asn Trp<br>                  420                        425                        430 | 1296 |
| gag gca gga aat act ttc acc tgc tct gtg tta cat gag ggc ctg cac<br>Glu Ala Gly Asn Thr Phe Thr Cys Ser Val Leu His Glu Gly Leu His<br>            435                        440                        445 | 1344 |
| aac cac cat act gag aag agc ctc tcc cac tct cct ggt aaa tga<br>Asn His His Thr Glu Lys Ser Leu Ser His Ser Pro Gly Lys<br>450                          455                        460 | 1389 |

-continued

```
<210> SEQ ID NO 2
<211> LENGTH: 462
<212> TYPE: PRT
<213> ORGANISM: Mus musculus

<400> SEQUENCE: 2
```

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ser Tyr Gly Val Asp Trp Val Arg Gln Pro Pro Gly Lys Gly Leu
    50                  55                  60

Glu Trp Leu Gly Val Ile Trp Gly Gly Ser Thr Asn Tyr Asn Ser
65              70                  75                  80

Ala Leu Met Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Met Tyr
            100                 105                 110

Tyr Cys Ala Lys His Glu Val Leu Arg Gly Tyr Ala Leu Asp Tyr Trp
        115                 120                 125

Gly Gln Gly Thr Ser Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

```
Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
                420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
        450                 455                 460

<210> SEQ ID NO 3
<211> LENGTH: 708
<212> TYPE: DNA
<213> ORGANISM: Mus musculus
<220> FEATURE:
<221> NAME/KEY: CDS
<222> LOCATION: (1)..(708)
<223> OTHER INFORMATION: light chain

<400> SEQUENCE: 3
```

| | | | | | | | | | | | | | | | | |
|---|---|---|---|---|---|---|---|---|---|---|---|---|---|---|---|---|
| atg | gat | ttt | caa | gtg | cag | att | ttc | agc | ttc | ctg | cta | atc | agt | gcc | tca | 48 |
| Met | Asp | Phe | Gln | Val | Gln | Ile | Phe | Ser | Phe | Leu | Leu | Ile | Ser | Ala | Ser | |
| 1 | | | | 5 | | | | | 10 | | | | | 15 | | |
| gtc | ata | atg | tcc | aga | gga | gaa | aat | gtt | ctc | acc | cag | tct | cca | gca | atc | 96 |
| Val | Ile | Met | Ser | Arg | Gly | Glu | Asn | Val | Leu | Thr | Gln | Ser | Pro | Ala | Ile | |
| | | | 20 | | | | | 25 | | | | | 30 | | | |
| atg | tct | gca | tct | cca | ggg | gaa | aag | gtc | acc | atg | acc | tgc | agt | gcc | agc | 144 |
| Met | Ser | Ala | Ser | Pro | Gly | Glu | Lys | Val | Thr | Met | Thr | Cys | Ser | Ala | Ser | |
| | | | 35 | | | | | 40 | | | | | 45 | | | |
| tca | agt | gta | agt | tac | atg | cac | tgg | tac | cag | cag | aag | tca | aac | acc | tcc | 192 |
| Ser | Ser | Val | Ser | Tyr | Met | His | Trp | Tyr | Gln | Gln | Lys | Ser | Asn | Thr | Ser | |
| | 50 | | | | | 55 | | | | | 60 | | | | | |
| ccc | aaa | ctc | tgg | att | tat | gac | aca | tcc | aaa | ctg | gct | tct | gga | gtc | cca | 240 |
| Pro | Lys | Leu | Trp | Ile | Tyr | Asp | Thr | Ser | Lys | Leu | Ala | Ser | Gly | Val | Pro | |
| 65 | | | | | 70 | | | | | 75 | | | | | 80 | |
| ggt | cgc | ttc | agt | ggc | agg | ggg | tct | gga | aac | tct | tat | tct | ctc | acg | atc | 288 |
| Gly | Arg | Phe | Ser | Gly | Arg | Gly | Ser | Gly | Asn | Ser | Tyr | Ser | Leu | Thr | Ile | |
| | | | 85 | | | | | 90 | | | | | 95 | | | |
| agc | agc | atg | gag | gct | gaa | gat | gtt | gcc | act | tat | tac | tgt | ttt | cag | ggg | 336 |
| Ser | Ser | Met | Glu | Ala | Glu | Asp | Val | Ala | Thr | Tyr | Tyr | Cys | Phe | Gln | Gly | |
| | | | 100 | | | | | 105 | | | | | 110 | | | |
| agt | ggg | tac | cca | ctc | acg | ttc | ggc | tcg | ggg | aca | aag | ttg | gaa | ata | aaa | 384 |
| Ser | Gly | Tyr | Pro | Leu | Thr | Phe | Gly | Ser | Gly | Thr | Lys | Leu | Glu | Ile | Lys | |
| | | | 115 | | | | | 120 | | | | | 125 | | | |
| cgg | gct | gat | gct | gca | cca | act | gta | tcc | atc | ttc | cca | cca | tcc | agt | gag | 432 |
| Arg | Ala | Asp | Ala | Ala | Pro | Thr | Val | Ser | Ile | Phe | Pro | Pro | Ser | Ser | Glu | |
| | 130 | | | | | 135 | | | | | 140 | | | | | |
| cag | tta | aca | tct | gga | ggt | gcc | tca | gtc | gtg | tgc | ttc | ttg | aac | aac | ttc | 480 |
| Gln | Leu | Thr | Ser | Gly | Gly | Ala | Ser | Val | Val | Cys | Phe | Leu | Asn | Asn | Phe | |
| 145 | | | | | 150 | | | | | 155 | | | | | 160 | |
| tac | ccc | aaa | gac | atc | aat | gtc | aag | tgg | aag | att | gat | ggc | agt | gaa | cga | 528 |
| Tyr | Pro | Lys | Asp | Ile | Asn | Val | Lys | Trp | Lys | Ile | Asp | Gly | Ser | Glu | Arg | |
| | | | 165 | | | | | 170 | | | | | 175 | | | |
| caa | aat | ggc | gtc | ctg | aac | agt | tgg | act | gat | cag | gac | agc | aaa | gac | agc | 576 |
| Gln | Asn | Gly | Val | Leu | Asn | Ser | Trp | Thr | Asp | Gln | Asp | Ser | Lys | Asp | Ser | |
| | | | 180 | | | | | 185 | | | | | 190 | | | |
| acc | tac | agc | atg | agc | agc | acc | ctc | acg | ttg | acc | aag | gac | gag | tat | gaa | 624 |
| Thr | Tyr | Ser | Met | Ser | Ser | Thr | Leu | Thr | Leu | Thr | Lys | Asp | Glu | Tyr | Glu | |
| | | | 195 | | | | | 200 | | | | | 205 | | | |

```
cga cat aac agc tat acc tgt gag gcc act cac aag aca tca act tca    672
Arg His Asn Ser Tyr Thr Cys Glu Ala Thr His Lys Thr Ser Thr Ser
    210                 215                 220 ccc att gtc aag agc ttc aac agg aat gag tgt tag                    708
Pro Ile Val Lys Ser Phe Asn Arg Asn Glu Cys
225                 230                 235
```

<210> SEQ ID NO 4
<211> LENGTH: 235
<212> TYPE: PRT
<213> ORGANISM: Mus musculus

<400> SEQUENCE: 4

```
Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met His Trp Tyr Gln Gln Lys Ser Asn Thr Ser
    50                  55                  60

Pro Lys Leu Trp Ile Tyr Asp Thr Ser Lys Leu Ala Ser Gly Val Pro
65                  70                  75                  80

Gly Arg Phe Ser Gly Arg Gly Ser Gly Asn Ser Tyr Ser Leu Thr Ile
                85                  90                  95

Ser Ser Met Glu Ala Glu Asp Val Ala Thr Tyr Tyr Cys Phe Gln Gly
            100                 105                 110

Ser Gly Tyr Pro Leu Thr Phe Gly Ser Gly Thr Lys Leu Glu Ile Lys
        115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 5
<211> LENGTH: 1410
<212> TYPE: DNA
<213> ORGANISM: Mus musculus
<220> FEATURE:
<221> NAME/KEY: CDS
<222> LOCATION: (1)..(1410)
<223> OTHER INFORMATION: heavy chain

<400> SEQUENCE: 5

```
atg gct gtc ctg gtg ctg ttc ctc tgc ctg gtt gca ttt cca agc tgt    48
Met Ala Val Leu Val Leu Phe Leu Cys Leu Val Ala Phe Pro Ser Cys
1               5                   10                  15
```

| | | |
|---|---|---|
| gtc ctg acc cag gtg cag ctg aag gag tca gga cct ggc ctg gtg gcg<br>Val Leu Thr Gln Val Gln Leu Lys Glu Ser Gly Pro Gly Leu Val Ala<br>20　　　　　　　　25　　　　　　　　30 | 96 | |
| ccc tca cag agc ctg tcc atc act tgc act gtc tct ggg ttt tca tta<br>Pro Ser Gln Ser Leu Ser Ile Thr Cys Thr Val Ser Gly Phe Ser Leu<br>　　35　　　　　　　　40　　　　　　　　45 | 144 | |
| gcc agc tat ggt gta gac tgg gtt cgc cag cct cca gga aag ggt ctg<br>Ala Ser Tyr Gly Val Asp Trp Val Arg Gln Pro Pro Gly Lys Gly Leu<br>50　　　　　　　　55　　　　　　　　60 | 192 | |
| gag tgg ctg gga gta ata tgg ggt ggt gga agt aca aat tat aat tca<br>Glu Trp Leu Gly Val Ile Trp Gly Gly Gly Ser Thr Asn Tyr Asn Ser<br>65　　　　　　70　　　　　　　　75　　　　　　　　80 | 240 | |
| gct ctc atg tcc aga ctt acc atc aac aaa gac aac tcc aag agc caa<br>Ala Leu Met Ser Arg Leu Thr Ile Asn Lys Asp Asn Ser Lys Ser Gln<br>　　　　85　　　　　　　　90　　　　　　　　95 | 288 | |
| ctt ttc tta aaa atg aac agt ctg caa act gat gac aca gcc atg tat<br>Leu Phe Leu Lys Met Asn Ser Leu Gln Thr Asp Asp Thr Ala Met Tyr<br>　　　　　100　　　　　　　　105　　　　　　　110 | 336 | |
| tac tgt gcc aaa cat gga gat agt aat tcc ggt tat gct atg gac tac<br>Tyr Cys Ala Lys His Gly Asp Ser Asn Ser Gly Tyr Ala Met Asp Tyr<br>　　　　　115　　　　　　　　120　　　　　　　　125 | 384 | |
| tgg ggt caa gga atc tca gtc acc gtc tcc tca gct aca aca aca gcc<br>Trp Gly Gln Gly Ile Ser Val Thr Val Ser Ser Ala Thr Thr Thr Ala<br>130　　　　　　　135　　　　　　　　140 | 432 | |
| cca tct gtc tat ccc ttg gtc cct ggc tgc ggt gac aca tct gga tcc<br>Pro Ser Val Tyr Pro Leu Val Pro Gly Cys Gly Asp Thr Ser Gly Ser<br>145　　　　　　150　　　　　　　　155　　　　　　　　160 | 480 | |
| tcg gtg aca ctg gga tgc ctt gtc aaa ggc tac ttc cct gag ccg gta<br>Ser Val Thr Leu Gly Cys Leu Val Lys Gly Tyr Phe Pro Glu Pro Val<br>　　　　　165　　　　　　　　170　　　　　　　175 | 528 | |
| act gta aaa tgg aac tat gga gcc ctg tcc agc ggt gtg cgc aca gtc<br>Thr Val Lys Trp Asn Tyr Gly Ala Leu Ser Ser Gly Val Arg Thr Val<br>　　　　　180　　　　　　　　185　　　　　　　190 | 576 | |
| tca tct gta ctg cag tct ggg ttc tat tcc ctc agc agc ttg gtg act<br>Ser Ser Val Leu Gln Ser Gly Phe Tyr Ser Leu Ser Ser Leu Val Thr<br>　　　　　195　　　　　　　　200　　　　　　　205 | 624 | |
| gta ccc tcc agc acc tgg ccc agc cag act gtc atc tgc aac gta gcc<br>Val Pro Ser Ser Thr Trp Pro Ser Gln Thr Val Ile Cys Asn Val Ala<br>210　　　　　　　　215　　　　　　　　220 | 672 | |
| cac cca gcc agc aag act gag ttg atc aag aga atc gag cct aga ata<br>His Pro Ala Ser Lys Thr Glu Leu Ile Lys Arg Ile Glu Pro Arg Ile<br>225　　　　　　　230　　　　　　　235　　　　　　　240 | 720 | |
| ccc aag ccc agt acc ccc cca ggt tct tca tgc cca cct ggt aac atc<br>Pro Lys Pro Ser Thr Pro Pro Gly Ser Ser Cys Pro Pro Gly Asn Ile<br>　　　　　245　　　　　　　　250　　　　　　　255 | 768 | |
| ttg ggt gga cca tcc gtc ttc atc ttc ccc cca aag ccc aag gat gca<br>Leu Gly Gly Pro Ser Val Phe Ile Phe Pro Pro Lys Pro Lys Asp Ala<br>　　　　　260　　　　　　　　265　　　　　　　270 | 816 | |
| ctc atg atc tcc cta acc ccc aag gtt acg tgt gtg gtg gtg gat gtg<br>Leu Met Ile Ser Leu Thr Pro Lys Val Thr Cys Val Val Val Asp Val<br>　　　　　275　　　　　　　　280　　　　　　　285 | 864 | |
| agc gag gat gac cca gat gtc cat gtc agc tgg ttt gtg gac aac aaa<br>Ser Glu Asp Asp Pro Asp Val His Val Ser Trp Phe Val Asp Asn Lys<br>290　　　　　　　　295　　　　　　　　300 | 912 | |
| gaa gta cac aca gcc tgg acg cag ccc cgt gaa gct cag tac aac agt<br>Glu Val His Thr Ala Trp Thr Gln Pro Arg Glu Ala Gln Tyr Asn Ser<br>305　　　　　　　310　　　　　　　　315　　　　　　　320 | 960 | |
| acc ttc cga gtg gtc agt gcc ctc ccc atc cag cac cag gac tgg atg<br>Thr Phe Arg Val Val Ser Ala Leu Pro Ile Gln His Gln Asp Trp Met<br>　　　　　325　　　　　　　　330　　　　　　　335 | 1008 | |

```
agg ggc aag gag ttc aaa tgc aag gtc aac aac aaa gcc ctc cca gcc    1056
Arg Gly Lys Glu Phe Lys Cys Lys Val Asn Asn Lys Ala Leu Pro Ala
            340                 345                 350 ccc atc gag aga acc atc tca aaa ccc aaa gga aga gcc cag aca cct    1104
Pro Ile Glu Arg Thr Ile Ser Lys Pro Lys Gly Arg Ala Gln Thr Pro
            355                 360                 365 caa gta tac acc ata ccc cca cct cgt gaa caa atg tcc aag aag aag    1152
Gln Val Tyr Thr Ile Pro Pro Pro Arg Glu Gln Met Ser Lys Lys Lys
        370                 375                 380 gtt agt ctg acc tgc ctg gtc acc aac ttc ttc tct gaa gcc atc agt    1200
Val Ser Leu Thr Cys Leu Val Thr Asn Phe Phe Ser Glu Ala Ile Ser
385                 390                 395                 400 gtg gag tgg gaa agg aac gga gaa ctg gag cag gat tac aag aac act    1248
Val Glu Trp Glu Arg Asn Gly Glu Leu Glu Gln Asp Tyr Lys Asn Thr
                405                 410                 415 cca ccc atc ctg gac tcg gat ggg acc tac ttc ctc tac agc aag ctc    1296
Pro Pro Ile Leu Asp Ser Asp Gly Thr Tyr Phe Leu Tyr Ser Lys Leu
                420                 425                 430 act gtg gat aca gac agt tgg ttg caa gga gaa att ttt acc tgc tcc    1344
Thr Val Asp Thr Asp Ser Trp Leu Gln Gly Glu Ile Phe Thr Cys Ser
            435                 440                 445 gtg gtg cat gag gct ctc cat aac cac cac aca cag aag aac ctg tct    1392
Val Val His Glu Ala Leu His Asn His His Thr Gln Lys Asn Leu Ser
        450                 455                 460 cgc tcc cct ggt aaa tga                                            1410
Arg Ser Pro Gly Lys
465

<210> SEQ ID NO 6
<211> LENGTH: 469
<212> TYPE: PRT
<213> ORGANISM: Mus musculus

<400> SEQUENCE: 6

Met Ala Val Leu Val Leu Phe Leu Cys Leu Val Ala Phe Pro Ser Cys
1               5                   10                  15

Val Leu Thr Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Ala Ser Tyr Gly Val Asp Trp Val Arg Gln Pro Pro Gly Lys Gly Leu
    50                  55                  60

Glu Trp Leu Gly Val Ile Trp Gly Gly Gly Ser Thr Asn Tyr Asn Ser
65                  70                  75                  80

Ala Leu Met Ser Arg Leu Thr Ile Asn Lys Asp Asn Ser Lys Ser Gln
                85                  90                  95

Leu Phe Leu Lys Met Asn Ser Leu Gln Thr Asp Asp Thr Ala Met Tyr
            100                 105                 110

Tyr Cys Ala Lys His Gly Asp Ser Asn Ser Gly Tyr Ala Met Asp Tyr
        115                 120                 125

Trp Gly Gln Gly Ile Ser Val Thr Val Ser Ser Ala Thr Thr Thr Ala
    130                 135                 140

Pro Ser Val Tyr Pro Leu Val Pro Gly Cys Gly Asp Thr Ser Gly Ser
145                 150                 155                 160

Ser Val Thr Leu Gly Cys Leu Val Lys Gly Tyr Phe Pro Glu Pro Val
                165                 170                 175

Thr Val Lys Trp Asn Tyr Gly Ala Leu Ser Ser Gly Val Arg Thr Val
            180                 185                 190
```

```
Ser Ser Val Leu Gln Ser Gly Phe Tyr Ser Leu Ser Ser Leu Val Thr
            195                 200                 205

Val Pro Ser Ser Thr Trp Pro Ser Gln Thr Val Ile Cys Asn Val Ala
    210                 215                 220

His Pro Ala Ser Lys Thr Glu Leu Ile Lys Arg Ile Glu Pro Arg Ile
225                 230                 235                 240

Pro Lys Pro Ser Thr Pro Pro Gly Ser Ser Cys Pro Pro Gly Asn Ile
                245                 250                 255

Leu Gly Gly Pro Ser Val Phe Ile Phe Pro Pro Lys Pro Lys Asp Ala
                260                 265                 270

Leu Met Ile Ser Leu Thr Pro Lys Val Thr Cys Val Val Val Asp Val
            275                 280                 285

Ser Glu Asp Asp Pro Asp Val His Val Ser Trp Phe Val Asp Asn Lys
    290                 295                 300

Glu Val His Thr Ala Trp Thr Gln Pro Arg Glu Ala Gln Tyr Asn Ser
305                 310                 315                 320

Thr Phe Arg Val Val Ser Ala Leu Pro Ile Gln His Gln Asp Trp Met
                325                 330                 335

Arg Gly Lys Glu Phe Lys Cys Lys Val Asn Asn Lys Ala Leu Pro Ala
                340                 345                 350

Pro Ile Glu Arg Thr Ile Ser Lys Pro Lys Gly Arg Ala Gln Thr Pro
            355                 360                 365

Gln Val Tyr Thr Ile Pro Pro Arg Glu Gln Met Ser Lys Lys Lys
    370                 375                 380

Val Ser Leu Thr Cys Leu Val Thr Asn Phe Phe Ser Glu Ala Ile Ser
385                 390                 395                 400

Val Glu Trp Glu Arg Asn Gly Glu Leu Glu Gln Asp Tyr Lys Asn Thr
                405                 410                 415

Pro Pro Ile Leu Asp Ser Asp Gly Thr Tyr Phe Leu Tyr Ser Lys Leu
                420                 425                 430

Thr Val Asp Thr Asp Ser Trp Leu Gln Gly Glu Ile Phe Thr Cys Ser
            435                 440                 445

Val Val His Glu Ala Leu His Asn His Thr Gln Lys Asn Leu Ser
    450                 455                 460

Arg Ser Pro Gly Lys
465

<210> SEQ ID NO 7
<211> LENGTH: 708
<212> TYPE: DNA
<213> ORGANISM: Mus musculus
<220> FEATURE:
<221> NAME/KEY: CDS
<222> LOCATION: (1)..(708)
<223> OTHER INFORMATION: light chain

<400> SEQUENCE: 7 atg gat ttt caa gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tcc aga gga gaa aat gtt ctc acc cag tct cca gca atc      96
Val Ile Met Ser Arg Gly Glu Asn Val Leu Thr Gln Ser Pro Ala Ile
            20                  25                  30 atg tct gca tct cca ggg gaa aag gtc acc atg acc tgc agt gcc agc     144
Met Ser Ala Ser Pro Gly Glu Lys Val Thr Met Thr Cys Ser Ala Ser
        35                  40                  45
```

-continued

| | | |
|---|---|---|
| cca agt gta agt tac atg cac tgg tac cag cag aag tca agc acc tcc<br>Pro Ser Val Ser Tyr Met His Trp Tyr Gln Gln Lys Ser Ser Thr Ser<br>50 55 60 | | 192 |
| ccc aaa ctc tgg att tat gac aca tac aaa ctg gct tct gga gtc cca<br>Pro Lys Leu Trp Ile Tyr Asp Thr Tyr Lys Leu Ala Ser Gly Val Pro<br>65 70 75 80 | | 240 |
| ggt cgc ttc agt ggc agt ggg tct gga aac tct tac tct ctc acg atc<br>Gly Arg Phe Ser Gly Ser Gly Ser Gly Asn Ser Tyr Ser Leu Thr Ile<br>85 90 95 | | 288 |
| aga acc atg gag gct gaa gat gtt gcc act tat tac tgt ttt cag ggg<br>Arg Thr Met Glu Ala Glu Asp Val Ala Thr Tyr Tyr Cys Phe Gln Gly<br>100 105 110 | | 336 |
| agt ggg ttc cca ctc acg ttc ggc tcg ggg aca aag ttg gaa ata aaa<br>Ser Gly Phe Pro Leu Thr Phe Gly Ser Gly Thr Lys Leu Glu Ile Lys<br>115 120 125 | | 384 |
| cgg gct gat gct gca cca act gta tcc atc ttc cca cca tcc agt gag<br>Arg Ala Asp Ala Ala Pro Thr Val Ser Ile Phe Pro Pro Ser Ser Glu<br>130 135 140 | | 432 |
| cag tta aca tct gga ggt gcc tca gtc gtg tgc ttc ttg aac aac ttc<br>Gln Leu Thr Ser Gly Gly Ala Ser Val Val Cys Phe Leu Asn Asn Phe<br>145 150 155 160 | | 480 |
| tac ccc aaa gac atc aat gtc aag tgg aag att gat ggc agt gaa cga<br>Tyr Pro Lys Asp Ile Asn Val Lys Trp Lys Ile Asp Gly Ser Glu Arg<br>165 170 175 | | 528 |
| caa aat ggc gtc ctg aac agt tgg act gat cag gac agc aaa gac agc<br>Gln Asn Gly Val Leu Asn Ser Trp Thr Asp Gln Asp Ser Lys Asp Ser<br>180 185 190 | | 576 |
| acc tac agc atg agc agc acc ctc acg ttg acc aag gac gag tat gaa<br>Thr Tyr Ser Met Ser Ser Thr Leu Thr Leu Thr Lys Asp Glu Tyr Glu<br>195 200 205 | | 624 |
| cga cat aac agc tat acc tgt gag gcc act cac aag aca tca act tca<br>Arg His Asn Ser Tyr Thr Cys Glu Ala Thr His Lys Thr Ser Thr Ser<br>210 215 220 | | 672 |
| ccc att gtc aag agc ttc aac agg aat gag tgt tag<br>Pro Ile Val Lys Ser Phe Asn Arg Asn Glu Cys<br>225 230 235 | | 708 |

<210> SEQ ID NO 8
<211> LENGTH: 235
<212> TYPE: PRT
<213> ORGANISM: Mus musculus

<400> SEQUENCE: 8

Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Ile
                20                  25                  30

Met Ser Ala Ser Pro Gly Glu Lys Val Thr Met Thr Cys Ser Ala Ser
            35                  40                  45

Pro Ser Val Ser Tyr Met His Trp Tyr Gln Gln Lys Ser Ser Thr Ser
        50                  55                  60

Pro Lys Leu Trp Ile Tyr Asp Thr Tyr Lys Leu Ala Ser Gly Val Pro
65                  70                  75                  80

Gly Arg Phe Ser Gly Ser Gly Ser Gly Asn Ser Tyr Ser Leu Thr Ile
                85                  90                  95

Arg Thr Met Glu Ala Glu Asp Val Ala Thr Tyr Tyr Cys Phe Gln Gly
            100                 105                 110

Ser Gly Phe Pro Leu Thr Phe Gly Ser Gly Thr Lys Leu Glu Ile Lys
        115                 120                 125

```
Arg Ala Asp Ala Ala Pro Thr Val Ser Ile Phe Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 9
<211> LENGTH: 1407
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1407)
<223> OTHER INFORMATION: humanized heavy chain

<400> SEQUENCE: 9

```
atg gct gtc ctg gtg ctg ttc ctc tgc ctg gtt gca ttt cca agc tgt     48
Met Ala Val Leu Val Leu Phe Leu Cys Leu Val Ala Phe Pro Ser Cys
1               5                   10                  15 gtc ctg tcc cag gtg cag ctg cag gag tcg ggc cca gga ctg gtg aag     96
Val Leu Ser Gln Val Gln Leu Gln Glu Ser Gly Pro Gly Leu Val Lys
            20                  25                  30 cct tcg gag acc ctg tcc ctc acc tgc act gtc tct ggg ttt tca tta    144
Pro Ser Glu Thr Leu Ser Leu Thr Cys Thr Val Ser Gly Phe Ser Leu
        35                  40                  45 acc agc tat ggt gta gac tgg atc cgg cag ccc cca ggg aag gga ctg    192
Thr Ser Tyr Gly Val Asp Trp Ile Arg Gln Pro Pro Gly Lys Gly Leu
    50                  55                  60 gag tgg att ggg gta ata tgg ggt ggt gga agc aca aat tat aat tca    240
Glu Trp Ile Gly Val Ile Trp Gly Gly Gly Ser Thr Asn Tyr Asn Ser
65                  70                  75                  80 gct ctc atg tcc cga gtc acc ata tca gta gac acg tcc aag aac cag    288
Ala Leu Met Ser Arg Val Thr Ile Ser Val Asp Thr Ser Lys Asn Gln
                85                  90                  95 ttc tcc ctg aag ctg agc tct gtg acc gct gcg gac acg gcc gtg tat    336
Phe Ser Leu Lys Leu Ser Ser Val Thr Ala Ala Asp Thr Ala Val Tyr
            100                 105                 110 tac tgt gcg aga cat gag gta cta cgg ggg tat gct ctg gac tac tgg    384
Tyr Cys Ala Arg His Glu Val Leu Arg Gly Tyr Ala Leu Asp Tyr Trp
        115                 120                 125 ggc caa ggt acc ctg gtc acc gtc tcg agt gct agc acc aag ggc cca    432
Gly Gln Gly Thr Leu Val Thr Val Ser Ser Ala Ser Thr Lys Gly Pro
    130                 135                 140 tcg gtc ttc ccc ctg gca ccc tcc tcc aag agc acc tct ggg ggc aca    480
Ser Val Phe Pro Leu Ala Pro Ser Ser Lys Ser Thr Ser Gly Gly Thr
145                 150                 155                 160 gcg gcc ctg ggc tgc ctg gtc aag gac tac ttc ccc gaa ccg gtg acg    528
Ala Ala Leu Gly Cys Leu Val Lys Asp Tyr Phe Pro Glu Pro Val Thr
                165                 170                 175
```

```
gtg tcg tgg aac tca ggc gcc ctg acc agc ggc gtg cac acc ttc ccg      576
Val Ser Trp Asn Ser Gly Ala Leu Thr Ser Gly Val His Thr Phe Pro
            180                 185                 190 gct gtc cta cag tcc tca gga ctc tac tcc ctc agc agc gtg gtg acc      624
Ala Val Leu Gln Ser Ser Gly Leu Tyr Ser Leu Ser Ser Val Val Thr
                195                 200                 205 gtg ccc tcc agc agc ttg ggc acc cag acc tac atc tgc aac gtg aat      672
Val Pro Ser Ser Ser Leu Gly Thr Gln Thr Tyr Ile Cys Asn Val Asn
210                 215                 220 cac aag ccc agc aac acc aag gtg gac aag aga gtt gag ccc aaa tct      720
His Lys Pro Ser Asn Thr Lys Val Asp Lys Arg Val Glu Pro Lys Ser
225                 230                 235                 240 tgt gac aaa act cac aca tgc cca ccg tgc cca gca cct gaa ctc ctg      768
Cys Asp Lys Thr His Thr Cys Pro Pro Cys Pro Ala Pro Glu Leu Leu
                245                 250                 255 ggg gga ccg tca gtc ttc ctc ttc ccc cca aaa ccc aag gac acc ctc      816
Gly Gly Pro Ser Val Phe Leu Phe Pro Pro Lys Pro Lys Asp Thr Leu
                260                 265                 270 atg atc tcc cgg acc cct gag gtc aca tgc gtg gtg gtg gac gtg agc      864
Met Ile Ser Arg Thr Pro Glu Val Thr Cys Val Val Val Asp Val Ser
            275                 280                 285 cac gaa gac cct gag gtc aag ttc aac tgg tac gtg gac ggc gtg gag      912
His Glu Asp Pro Glu Val Lys Phe Asn Trp Tyr Val Asp Gly Val Glu
            290                 295                 300 gtg cat aat gcc aag aca aag ccg cgg gag gag cag tac aac agc acg      960
Val His Asn Ala Lys Thr Lys Pro Arg Glu Glu Gln Tyr Asn Ser Thr
305                 310                 315                 320 tac cgt gtg gtc agc gtc ctc acc gtc ctg cac cag gac tgg ctg aat     1008
Tyr Arg Val Val Ser Val Leu Thr Val Leu His Gln Asp Trp Leu Asn
                325                 330                 335 ggc aag gag tac aag tgc aag gtc tcc aac aaa gcc ctc cca gcc ccc     1056
Gly Lys Glu Tyr Lys Cys Lys Val Ser Asn Lys Ala Leu Pro Ala Pro
                340                 345                 350 atc gag aaa acc atc tcc aaa gcc aaa ggg cag ccc cga gaa cca cag     1104
Ile Glu Lys Thr Ile Ser Lys Ala Lys Gly Gln Pro Arg Glu Pro Gln
            355                 360                 365 gtg tac acc ctg ccc cca tcc cgg gat gag ctg acc aag aac cag gtc     1152
Val Tyr Thr Leu Pro Pro Ser Arg Asp Glu Leu Thr Lys Asn Gln Val
            370                 375                 380 agc ctg acc tgc ctg gtc aaa ggc ttc tat ccc agc gac atc gcc gtg     1200
Ser Leu Thr Cys Leu Val Lys Gly Phe Tyr Pro Ser Asp Ile Ala Val
385                 390                 395                 400 gag tgg gag agc aat ggg cag ccg gag aac aac tac aag acc acg cct     1248
Glu Trp Glu Ser Asn Gly Gln Pro Glu Asn Asn Tyr Lys Thr Thr Pro
                405                 410                 415 ccc gtg ctg gac tcc gac ggc tcc ttc ttc ctc tac agc aag ctc acc     1296
Pro Val Leu Asp Ser Asp Gly Ser Phe Phe Leu Tyr Ser Lys Leu Thr
                420                 425                 430 gtg gac aag agc agg tgg cag cag ggg aac gtc ttc tca tgc tcc gtg     1344
Val Asp Lys Ser Arg Trp Gln Gln Gly Asn Val Phe Ser Cys Ser Val
            435                 440                 445 atg cat gag gct ctg cac aac cac tac acg cag aag agc ctc tcc ctg     1392
Met His Glu Ala Leu His Asn His Tyr Thr Gln Lys Ser Leu Ser Leu
450                 455                 460 tct ccg ggt aaa tga                                                  1407
Ser Pro Gly Lys
465
```

<210> SEQ ID NO 10
<211> LENGTH: 468
<212> TYPE: PRT
<213> ORGANISM: Artificial Sequence
<220> FEATURE:
<223> OTHER INFORMATION: Synthetic Construct

<400> SEQUENCE: 10

```
Met Ala Val Leu Val Leu Phe Leu Cys Leu Ala Phe Pro Ser Cys
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Thr Ser Tyr Gly Val Asp Trp Ile Arg Gln Pro Pro Gly Lys Gly Leu
    50                  55                  60

Glu Trp Ile Gly Val Ile Trp Gly Gly Gly Ser Thr Asn Tyr Asn Ser
65                  70                  75                  80

Ala Leu Met Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg His Glu Val Leu Arg Gly Tyr Ala Leu Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365
```

```
Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 11
<211> LENGTH: 1407
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1407)
<223> OTHER INFORMATION: humanized heavy chain

<400> SEQUENCE: 11 atg gct gtc ctg gtg ctg ttc ctc tgc ctg gtt gca ttt cca agc tgt        48
Met Ala Val Leu Val Leu Phe Leu Cys Leu Val Ala Phe Pro Ser Cys
1               5                   10                  15 gtc ctg tcc cag gtg cag ctg cag gag tcg ggc cca gga ctg gtg aag        96
Val Leu Ser Gln Val Gln Leu Gln Glu Ser Gly Pro Gly Leu Val Lys
            20                  25                  30 cct tcg gag acc ctg tcc ctc acc tgc act gtc tct ggg ttt tca tta       144
Pro Ser Glu Thr Leu Ser Leu Thr Cys Thr Val Ser Gly Phe Ser Leu
        35                  40                  45 acc agc tat ggt gta gac tgg atc cgg cag ccc cca ggg aag gga ctg       192
Thr Ser Tyr Gly Val Asp Trp Ile Arg Gln Pro Pro Gly Lys Gly Leu
    50                  55                  60 gag tgg att ggg gta ata tgg ggt ggt gga agc aca aat tat aat tca       240
Glu Trp Ile Gly Val Ile Trp Gly Gly Gly Ser Thr Asn Tyr Asn Ser
65                  70                  75                  80 tcc ctc atg tcc cga gtc acc ata tca aaa gac acg tcc aag aac cag       288
Ser Leu Met Ser Arg Val Thr Ile Ser Lys Asp Thr Ser Lys Asn Gln
                85                  90                  95 gtt tcc ctg aag ctg agc tct gtg acc gct gcg gac acg gcc gtg tat       336
Val Ser Leu Lys Leu Ser Ser Val Thr Ala Ala Asp Thr Ala Val Tyr
            100                 105                 110 tac tgt gcg aaa cat gag gta cta cgg ggg tat gct ctg gac tac tgg       384
Tyr Cys Ala Lys His Glu Val Leu Arg Gly Tyr Ala Leu Asp Tyr Trp
        115                 120                 125 ggc caa ggt acc ctg gtc acc gtc tcg agt gct agc acc aag ggc cca       432
Gly Gln Gly Thr Leu Val Thr Val Ser Ser Ala Ser Thr Lys Gly Pro
    130                 135                 140 tcg gtc ttc ccc ctg gca ccc tcc tcc aag agc acc tct ggg ggc aca       480
Ser Val Phe Pro Leu Ala Pro Ser Ser Lys Ser Thr Ser Gly Gly Thr
145                 150                 155                 160 gcg gcc ctg ggc tgc ctg gtc aag gac tac ttc ccc gaa ccg gtg acg       528
Ala Ala Leu Gly Cys Leu Val Lys Asp Tyr Phe Pro Glu Pro Val Thr
                165                 170                 175
```

-continued

```
gtg tcg tgg aac tca ggc gcc ctg acc agc ggc gtg cac acc ttc ccg        576
Val Ser Trp Asn Ser Gly Ala Leu Thr Ser Gly Val His Thr Phe Pro
            180                 185                 190 gct gtc cta cag tcc tca gga ctc tac tcc ctc agc agc gtg gtg acc        624
Ala Val Leu Gln Ser Ser Gly Leu Tyr Ser Leu Ser Ser Val Val Thr
                195                 200                 205 gtg ccc tcc agc agc ttg ggc acc cag acc tac atc tgc aac gtg aat        672
Val Pro Ser Ser Ser Leu Gly Thr Gln Thr Tyr Ile Cys Asn Val Asn
    210                 215                 220 cac aag ccc agc aac acc aag gtg gac aag aga gtt gag ccc aaa tct        720
His Lys Pro Ser Asn Thr Lys Val Asp Lys Arg Val Glu Pro Lys Ser
225                 230                 235                 240 tgt gac aaa act cac aca tgc cca ccg tgc cca gca cct gaa ctc ctg        768
Cys Asp Lys Thr His Thr Cys Pro Pro Cys Pro Ala Pro Glu Leu Leu
                245                 250                 255 ggg gga ccg tca gtc ttc ctc ttc ccc cca aaa ccc aag gac acc ctc        816
Gly Gly Pro Ser Val Phe Leu Phe Pro Pro Lys Pro Lys Asp Thr Leu
                260                 265                 270 atg atc tcc cgg acc cct gag gtc aca tgc gtg gtg gtg gac gtg agc        864
Met Ile Ser Arg Thr Pro Glu Val Thr Cys Val Val Val Asp Val Ser
    275                 280                 285 cac gaa gac cct gag gtc aag ttc aac tgg tac gtg gac ggc gtg gag        912
His Glu Asp Pro Glu Val Lys Phe Asn Trp Tyr Val Asp Gly Val Glu
290                 295                 300 gtg cat aat gcc aag aca aag ccg cgg gag gag cag tac aac agc acg        960
Val His Asn Ala Lys Thr Lys Pro Arg Glu Glu Gln Tyr Asn Ser Thr
305                 310                 315                 320 tac cgt gtg gtc agc gtc ctc acc gtc ctg cac cag gac tgg ctg aat       1008
Tyr Arg Val Val Ser Val Leu Thr Val Leu His Gln Asp Trp Leu Asn
                325                 330                 335 ggc aag gag tac aag tgc aag gtc tcc aac aaa gcc ctc cca gcc ccc       1056
Gly Lys Glu Tyr Lys Cys Lys Val Ser Asn Lys Ala Leu Pro Ala Pro
                340                 345                 350 atc gag aaa acc atc tcc aaa gcc aaa ggg cag ccc cga gaa cca cag       1104
Ile Glu Lys Thr Ile Ser Lys Ala Lys Gly Gln Pro Arg Glu Pro Gln
                355                 360                 365 gtg tac acc ctg ccc cca tcc cgg gat gag ctg acc aag aac cag gtc       1152
Val Tyr Thr Leu Pro Pro Ser Arg Asp Glu Leu Thr Lys Asn Gln Val
370                 375                 380 agc ctg acc tgc ctg gtc aaa ggc ttc tat ccc agc gac atc gcc gtg       1200
Ser Leu Thr Cys Leu Val Lys Gly Phe Tyr Pro Ser Asp Ile Ala Val
385                 390                 395                 400 gag tgg gag agc aat ggg cag ccg gag aac aac tac aag acc acg cct       1248
Glu Trp Glu Ser Asn Gly Gln Pro Glu Asn Asn Tyr Lys Thr Thr Pro
                405                 410                 415 ccc gtg ctg gac tcc gac ggc tcc ttc ttc ctc tac agc aag ctc acc       1296
Pro Val Leu Asp Ser Asp Gly Ser Phe Phe Leu Tyr Ser Lys Leu Thr
                420                 425                 430 gtg gac aag agc agg tgg cag cag ggg aac gtc ttc tca tgc tcc gtg       1344
Val Asp Lys Ser Arg Trp Gln Gln Gly Asn Val Phe Ser Cys Ser Val
                435                 440                 445 atg cat gag gct ctg cac aac cac tac acg cag aag agc ctc tcc ctg       1392
Met His Glu Ala Leu His Asn His Tyr Thr Gln Lys Ser Leu Ser Leu
    450                 455                 460 tct ccg ggt aaa tga                                                    1407
Ser Pro Gly Lys
465
```

<210> SEQ ID NO 12
<211> LENGTH: 468
<212> TYPE: PRT
<213> ORGANISM: Artificial Sequence
<220> FEATURE:
<223> OTHER INFORMATION: Synthetic Construct

<400> SEQUENCE: 12

```
Met Ala Val Leu Val Leu Phe Leu Cys Leu Ala Phe Pro Ser Cys
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
            35                  40                  45

Thr Ser Tyr Gly Val Asp Trp Ile Arg Gln Pro Pro Gly Lys Gly Leu
        50                  55                  60

Glu Trp Ile Gly Val Ile Trp Gly Gly Ser Thr Asn Tyr Asn Ser
65                  70                  75                  80

Ser Leu Met Ser Arg Val Thr Ile Ser Lys Asp Thr Ser Lys Asn Gln
                85                  90                  95

Val Ser Leu Lys Leu Ser Ser Val Thr Ala Ala Asp Thr Ala Val Tyr
            100                 105                 110

Tyr Cys Ala Lys His Glu Val Leu Arg Gly Tyr Ala Leu Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365
```

```
Val Tyr Thr Leu Pro Pro Ser Arg Asp Glu Leu Thr Lys Asn Gln Val
    370             375                 380

Ser Leu Thr Cys Leu Val Lys Gly Phe Tyr Pro Ser Asp Ile Ala Val
385             390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 13
<211> LENGTH: 1407
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1407)
<223> OTHER INFORMATION: humanized heavy chain

<400> SEQUENCE: 13 atg gct gtc ctg gtg ctg ttc ctc tgc ctg gtt gca ttt cca agc tgt     48
Met Ala Val Leu Val Leu Phe Leu Cys Leu Val Ala Phe Pro Ser Cys
1               5                   10                  15 gtc ctg tcc cag gtg cag ctg cag gag tcg ggc cca gga ctg gtg aag     96
Val Leu Ser Gln Val Gln Leu Gln Glu Ser Gly Pro Gly Leu Val Lys
            20                  25                  30 cct tcg gag acc ctg tcc ctc acc tgc act gtc tct ggg ttt tca tta    144
Pro Ser Glu Thr Leu Ser Leu Thr Cys Thr Val Ser Gly Phe Ser Leu
        35                  40                  45 acc agc tat ggt gta gac tgg gtt cgg cag ccc cca ggg aag gga ctg    192
Thr Ser Tyr Gly Val Asp Trp Val Arg Gln Pro Pro Gly Lys Gly Leu
    50                  55                  60 gag tgg att ggg gta ata tgg ggt ggt gga agc aca aat tat aat tca    240
Glu Trp Ile Gly Val Ile Trp Gly Gly Gly Ser Thr Asn Tyr Asn Ser
65                  70                  75                  80 gct ctc atg tcc cga ctg acc ata tca aaa gac aac tcc aag agc cag    288
Ala Leu Met Ser Arg Leu Thr Ile Ser Lys Asp Asn Ser Lys Ser Gln
                85                  90                  95 gtt tcc ctg aag ctg agc tct gtg acc gct gcg gac acg gcc gtg tat    336
Val Ser Leu Lys Leu Ser Ser Val Thr Ala Ala Asp Thr Ala Val Tyr
            100                 105                 110 tac tgt gcg aaa cat gag gta cta cgg ggg tat gct ctg gac tac tgg    384
Tyr Cys Ala Lys His Glu Val Leu Arg Gly Tyr Ala Leu Asp Tyr Trp
        115                 120                 125 ggc caa ggt acc ctg gtc acc gtc tcg agt gct agc acc aag ggc cca    432
Gly Gln Gly Thr Leu Val Thr Val Ser Ser Ala Ser Thr Lys Gly Pro
    130                 135                 140 tcg gtc ttc ccc ctg gca ccc tcc tcc aag agc acc tct ggg ggc aca    480
Ser Val Phe Pro Leu Ala Pro Ser Ser Lys Ser Thr Ser Gly Gly Thr
145                 150                 155                 160 gcg gcc ctg ggc tgc ctg gtc aag gac tac ttc ccc gaa ccg gtg acg    528
Ala Ala Leu Gly Cys Leu Val Lys Asp Tyr Phe Pro Glu Pro Val Thr
                165                 170                 175
```

|  |  |
|---|---:|
| gtg tcg tgg aac tca ggc gcc ctg acc agc ggc gtg cac acc ttc ccg<br>Val Ser Trp Asn Ser Gly Ala Leu Thr Ser Gly Val His Thr Phe Pro<br>        180                        185                        190 | 576 |
| gct gtc cta cag tcc tca gga ctc tac tcc ctc agc agc gtg gtg acc<br>Ala Val Leu Gln Ser Ser Gly Leu Tyr Ser Leu Ser Ser Val Val Thr<br>               195                       200                   205 | 624 |
| gtg ccc tcc agc agc ttg ggc acc cag acc tac atc tgc aac gtg aat<br>Val Pro Ser Ser Ser Leu Gly Thr Gln Thr Tyr Ile Cys Asn Val Asn<br>210                        215                       220 | 672 |
| cac aag ccc agc aac acc aag gtg gac aag aga gtt gag ccc aaa tct<br>His Lys Pro Ser Asn Thr Lys Val Asp Lys Arg Val Glu Pro Lys Ser<br>225                       230                      235                   240 | 720 |
| tgt gac aaa act cac aca tgc cca ccg tgc cca gca cct gaa ctc ctg<br>Cys Asp Lys Thr His Thr Cys Pro Pro Cys Pro Ala Pro Glu Leu Leu<br>                          245                       250                   255 | 768 |
| ggg gga ccg tca gtc ttc ctc ttc ccc cca aaa ccc aag gac acc ctc<br>Gly Gly Pro Ser Val Phe Leu Phe Pro Pro Lys Pro Lys Asp Thr Leu<br>               260                       265                   270 | 816 |
| atg atc tcc cgg acc cct gag gtc aca tgc gtg gtg gtg gac gtg agc<br>Met Ile Ser Arg Thr Pro Glu Val Thr Cys Val Val Val Asp Val Ser<br>             275                       280                   285 | 864 |
| cac gaa gac cct gag gtc aag ttc aac tgg tac gtg gac ggc gtg gag<br>His Glu Asp Pro Glu Val Lys Phe Asn Trp Tyr Val Asp Gly Val Glu<br>         290                       295                   300 | 912 |
| gtg cat aat gcc aag aca aag ccg cgg gag gag cag tac aac agc acg<br>Val His Asn Ala Lys Thr Lys Pro Arg Glu Glu Gln Tyr Asn Ser Thr<br>305                       310                      315                   320 | 960 |
| tac cgt gtg gtc agc gtc ctc acc gtc ctg cac cag gac tgg ctg aat<br>Tyr Arg Val Val Ser Val Leu Thr Val Leu His Gln Asp Trp Leu Asn<br>                          325                       330                   335 | 1008 |
| ggc aag gag tac aag tgc aag gtc tcc aac aaa gcc ctc cca gcc ccc<br>Gly Lys Glu Tyr Lys Cys Lys Val Ser Asn Lys Ala Leu Pro Ala Pro<br>               340                       345                   350 | 1056 |
| atc gag aaa acc atc tcc aaa gcc aaa ggg cag ccc cga gaa cca cag<br>Ile Glu Lys Thr Ile Ser Lys Ala Lys Gly Gln Pro Arg Glu Pro Gln<br>         355                       360                   365 | 1104 |
| gtg tac acc ctg ccc cca tcc cgg gat gag ctg acc aag aac cag gtc<br>Val Tyr Thr Leu Pro Pro Ser Arg Asp Glu Leu Thr Lys Asn Gln Val<br>370                        375                      380 | 1152 |
| agc ctg acc tgc ctg gtc aaa ggc ttc tat ccc agc gac atc gcc gtg<br>Ser Leu Thr Cys Leu Val Lys Gly Phe Tyr Pro Ser Asp Ile Ala Val<br>385                        390                      395                   400 | 1200 |
| gag tgg gag agc aat ggg cag ccg gag aac aac tac aag acc acg cct<br>Glu Trp Glu Ser Asn Gly Gln Pro Glu Asn Asn Tyr Lys Thr Thr Pro<br>                          405                       410                   415 | 1248 |
| ccc gtg ctg gac tcc gac ggc tcc ttc ttc ctc tac agc aag ctc acc<br>Pro Val Leu Asp Ser Asp Gly Ser Phe Phe Leu Tyr Ser Lys Leu Thr<br>               420                       425                   430 | 1296 |
| gtg gac aag agc agg tgg cag cag ggg aac gtc ttc tca tgc tcc gtg<br>Val Asp Lys Ser Arg Trp Gln Gln Gly Asn Val Phe Ser Cys Ser Val<br>             435                       440                   445 | 1344 |
| atg cat gag gct ctg cac aac cac tac acg cag aag agc ctc tcc ctg<br>Met His Glu Ala Leu His Asn His Tyr Thr Gln Lys Ser Leu Ser Leu<br>450                       455                      460 | 1392 |
| tct ccg ggt aaa tga<br>Ser Pro Gly Lys<br>465 | 1407 |

```
<210> SEQ ID NO 14
<211> LENGTH: 468
<212> TYPE: PRT
<213> ORGANISM: Artificial Sequence
<220> FEATURE:
<223> OTHER INFORMATION: Synthetic Construct

<400> SEQUENCE: 14
```

Met Ala Val Leu Val Leu Phe Leu Cys Leu Ala Phe Pro Ser Cys
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Thr Ser Tyr Gly Val Asp Trp Val Arg Gln Pro Pro Gly Lys Gly Leu
    50                  55                  60

Glu Trp Ile Gly Val Ile Trp Gly Gly Gly Ser Thr Asn Tyr Asn Ser
65                  70                  75                  80

Ala Leu Met Ser Arg Leu Thr Ile Ser Lys Asp Asn Ser Lys Ser Gln
                85                  90                  95

Val Ser Leu Lys Leu Ser Ser Val Thr Ala Ala Asp Thr Ala Val Tyr
            100                 105                 110

Tyr Cys Ala Lys His Glu Val Leu Arg Gly Tyr Ala Leu Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

```
Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 15
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(708)
<223> OTHER INFORMATION: humanized light chain

<400> SEQUENCE: 15 atg gat ttt caa gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tcc aga gga gaa att gtg ttg aca cag tct cca gcc acc      96
Val Ile Met Ser Arg Gly Glu Ile Val Leu Thr Gln Ser Pro Ala Thr
                20                  25                  30 ctg tct ttg tct cca ggg gaa aga gcc acc ctc tcc tgc agt gcc agc     144
Leu Ser Leu Ser Pro Gly Glu Arg Ala Thr Leu Ser Cys Ser Ala Ser
            35                  40                  45 tca agt gta agt tac atg cac tgg tac caa cag aaa cct ggc cag gct     192
Ser Ser Val Ser Tyr Met His Trp Tyr Gln Gln Lys Pro Gly Gln Ala
        50                  55                  60 ccc agg ctc ctc atc tat gac aca tcc aaa ctg gct tct ggc atc cca     240
Pro Arg Leu Leu Ile Tyr Asp Thr Ser Lys Leu Ala Ser Gly Ile Pro
65                  70                  75                  80 gcc agg ttc agt ggc agt ggg tct ggg aca gac ttc act ctc acc atc     288
Ala Arg Phe Ser Gly Ser Gly Ser Gly Thr Asp Phe Thr Leu Thr Ile
                85                  90                  95 agc agc cta gag cct gaa gat ttt gca gtt tat tac tgt ttt cag ggg     336
Ser Ser Leu Glu Pro Glu Asp Phe Ala Val Tyr Tyr Cys Phe Gln Gly
                100                 105                 110 agt ggg tac cca ctc acg ttt ggc cag ggg acc aag gtg gaa atc aaa     384
Ser Gly Tyr Pro Leu Thr Phe Gly Gln Gly Thr Lys Val Glu Ile Lys
            115                 120                 125 cgt acg gtg gct gca cca tct gtc ttc atc ttc ccg cca tct gat gag     432
Arg Thr Val Ala Ala Pro Ser Val Phe Ile Phe Pro Pro Ser Asp Glu
130                 135                 140 cag ttg aaa tct gga act gcc tct gtt gtg tgc ctg ctg aat aac ttc     480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa     528
Tyr Pro Arg Glu Ala Lys Val Gln Trp Lys Val Asp Asn Ala Leu Gln
                165                 170                 175
```

```
tcg ggt aac tcc cag gag agt gtc aca gag cag gac agc aag gac agc     576
Ser Gly Asn Ser Gln Glu Ser Val Thr Glu Gln Asp Ser Lys Asp Ser
        180                 185                 190 acc tac agc ctc agc agc acc ctg acg ctg agc aaa gca gac tac gag     624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg     672
Lys His Lys Val Tyr Ala Cys Glu Val Thr His Gln Gly Leu Ser Ser
210                 215                 220 ccc gtc aca aag agc ttc aac agg gga gag tgt tag                     708
Pro Val Thr Lys Ser Phe Asn Arg Gly Glu Cys
225                 230                 235
```

<210> SEQ ID NO 16
<211> LENGTH: 235
<212> TYPE: PRT
<213> ORGANISM: Artificial Sequence
<220> FEATURE:
<223> OTHER INFORMATION: Synthetic Construct

<400> SEQUENCE: 16

```
Met Asp Phe Gln Val Gln Ile Phe Ser Phe Leu Leu Ile Ser Ala Ser
1               5                   10                  15

Val Ile Met Ser Arg Gly Glu Ile Val Leu Thr Gln Ser Pro Ala Thr
            20                  25                  30

Leu Ser Leu Ser Pro Gly Glu Arg Ala Thr Leu Ser Cys Ser Ala Ser
        35                  40                  45

Ser Ser Val Ser Tyr Met His Trp Tyr Gln Gln Lys Pro Gly Gln Ala
    50                  55                  60

Pro Arg Leu Leu Ile Tyr Asp Thr Ser Lys Leu Ala Ser Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Phe Gln Gly
            100                 105                 110

Ser Gly Tyr Pro Leu Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 17
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(708)
<223> OTHER INFORMATION: humanized light chain

<400> SEQUENCE: 17

```
atg gat ttt caa gtg cag att ttc agc ttc ctg cta atc agt gcc tca       48
Met Asp Phe Gln Val Gln Ile Phe Ser Phe Leu Leu Ile Ser Ala Ser
1               5                   10                  15 gtc ata atg tcc aga gga gaa aat gtg ttg aca cag tct cca gcc acc       96
Val Ile Met Ser Arg Gly Glu Asn Val Leu Thr Gln Ser Pro Ala Thr
            20                  25                  30 ctg tct ttg tct cca ggg gaa aga gcc acc ctc tcc tgc agt gcc agc      144
Leu Ser Leu Ser Pro Gly Glu Arg Ala Thr Leu Ser Cys Ser Ala Ser
        35                  40                  45 tca agt gta agt tac atg cac tgg tac caa cag aaa cct ggc cag gct      192
Ser Ser Val Ser Tyr Met His Trp Tyr Gln Gln Lys Pro Gly Gln Ala
    50                  55                  60 ccc agg ctc ctc atc tat gac aca tcc aaa ctg gct tct ggc atc cca      240
Pro Arg Leu Leu Ile Tyr Asp Thr Ser Lys Leu Ala Ser Gly Ile Pro
65                  70                  75                  80 gcc agg ttc agt ggc agt ggg tct ggg aac gac tat act ctc acc atc      288
Ala Arg Phe Ser Gly Ser Gly Ser Gly Asn Asp Tyr Thr Leu Thr Ile
                85                  90                  95 agc agc cta gag cct gaa gat ttt gca gtt tat tac tgt ttt cag ggg      336
Ser Ser Leu Glu Pro Glu Asp Phe Ala Val Tyr Tyr Cys Phe Gln Gly
            100                 105                 110 agt ggg tac cca ctc acg ttt ggc cag ggg acc aag gtg gaa atc aaa      384
Ser Gly Tyr Pro Leu Thr Phe Gly Gln Gly Thr Lys Val Glu Ile Lys
        115                 120                 125 cgt acg gtg gct gca cca tct gtc ttc atc ttc ccg cca tct gat gag      432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc      480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa      528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc      576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag      624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg      672
Lys His Lys Val Tyr Ala Cys Glu Val Thr His Gln Gly Leu Ser Ser
    210                 215                 220 ccc gtc aca aag agc ttc aac agg gga gag tgt tag                      708
Pro Val Thr Lys Ser Phe Asn Arg Gly Glu Cys
225                 230                 235
```

<210> SEQ ID NO 18
<211> LENGTH: 235
<212> TYPE: PRT
<213> ORGANISM: Artificial Sequence
<220> FEATURE:
<223> OTHER INFORMATION: Synthetic Construct

<400> SEQUENCE: 18

Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Thr
            20                  25                  30

Leu Ser Leu Ser Pro Gly Glu Arg Ala Thr Leu Ser Cys Ser Ala Ser
            35                  40                  45

Ser Ser Val Ser Tyr Met His Trp Tyr Gln Gln Lys Pro Gly Gln Ala
        50                  55                  60

Pro Arg Leu Leu Ile Tyr Asp Thr Ser Lys Leu Ala Ser Gly Ile Pro
65                  70                  75                  80

Ala Arg Phe Ser Gly Ser Gly Ser Gly Asn Asp Tyr Thr Leu Thr Ile
                85                  90                  95

Ser Ser Leu Glu Pro Glu Asp Phe Ala Val Tyr Tyr Cys Phe Gln Gly
            100                 105                 110

Ser Gly Tyr Pro Leu Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 19
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(708)
<223> OTHER INFORMATION: humanized light chain

<400> SEQUENCE: 19 atg gat ttt caa gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tcc aga gga gaa aat gtg ttg aca cag tct cca gcc acc      96
Val Ile Met Ser Arg Gly Glu Asn Val Leu Thr Gln Ser Pro Ala Thr
            20                  25                  30 ctg tct ttg tct cca ggg gaa aga gcc acc ctc tcc tgc agt gcc agc     144
Leu Ser Leu Ser Pro Gly Glu Arg Ala Thr Leu Ser Cys Ser Ala Ser
            35                  40                  45 tca agt gta agt tac atg cac tgg tac caa cag aaa cct ggc cag gct     192
Ser Ser Val Ser Tyr Met His Trp Tyr Gln Gln Lys Pro Gly Gln Ala
        50                  55                  60

```
ccc agg ctc tgg atc tat gac aca tcc aaa ctg gct tct ggc atc cca     240
Pro Arg Leu Trp Ile Tyr Asp Thr Ser Lys Leu Ala Ser Gly Ile Pro
 65                  70                  75                  80 gcc agg ttc agt ggc agg ggg tct ggg aac gac tat act ctc acc atc     288
Ala Arg Phe Ser Gly Arg Gly Ser Gly Asn Asp Tyr Thr Leu Thr Ile
             85                  90                  95 agc agc cta gag cct gaa gat ttt gca gtt tat tac tgt ttt cag ggg     336
Ser Ser Leu Glu Pro Glu Asp Phe Ala Val Tyr Tyr Cys Phe Gln Gly
            100                 105                 110 agt ggg tac cca ctc acg ttt ggc cag ggg acc aag gtg gaa atc aaa     384
Ser Gly Tyr Pro Leu Thr Phe Gly Gln Gly Thr Lys Val Glu Ile Lys
        115                 120                 125 cgt acg gtg gct gca cca tct gtc ttc atc ttc ccg cca tct gat gag     432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc     480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa     528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc     576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag     624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg     672
Lys His Lys Val Tyr Ala Cys Glu Val Thr His Gln Gly Leu Ser Ser
    210                 215                 220 ccc gtc aca aag agc ttc aac agg gga gag tgt tag                     708
Pro Val Thr Lys Ser Phe Asn Arg Gly Glu Cys
225                 230                 235

<210> SEQ ID NO 20
<211> LENGTH: 235
<212> TYPE: PRT
<213> ORGANISM: Artificial Sequence
<220> FEATURE:
<223> OTHER INFORMATION: Synthetic Construct

<400> SEQUENCE: 20

Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Thr
            20                  25                  30

Leu Ser Leu Ser Pro Gly Glu Arg Ala Thr Leu Ser Cys Ser Ala Ser
        35                  40                  45

Ser Ser Val Ser Tyr Met His Trp Tyr Gln Gln Lys Pro Gly Gln Ala
    50                  55                  60

Pro Arg Leu Trp Ile Tyr Asp Thr Ser Lys Leu Ala Ser Gly Ile Pro
65                  70                  75                  80

Ala Arg Phe Ser Gly Arg Gly Ser Gly Asn Asp Tyr Thr Leu Thr Ile
            85                  90                  95

Ser Ser Leu Glu Pro Glu Asp Phe Ala Val Tyr Tyr Cys Phe Gln Gly
        100                 105                 110

Ser Gly Tyr Pro Leu Thr Phe Gly Gln Gly Thr Lys Val Glu Ile Lys
    115                 120                 125
```

```
Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 21
<211> LENGTH: 1410
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1410)
<223> OTHER INFORMATION: humanized heavy chain

<400> SEQUENCE: 21

```
atg gct gtc ctg gtg ctg ttc ctc tgc ctg gtt gca ttt cca agc tgt      48
Met Ala Val Leu Val Leu Phe Leu Cys Leu Val Ala Phe Pro Ser Cys
1               5                   10                  15 gtc ctg acc cag gtg cag ctg cag gag tcg ggc cca gga ctg gtg aag      96
Val Leu Thr Gln Val Gln Leu Gln Glu Ser Gly Pro Gly Leu Val Lys
            20                  25                  30 cct tcg gag acc ctg tcc ctc acc tgc act gtc tct ggg ttt tca tta     144
Pro Ser Glu Thr Leu Ser Leu Thr Cys Thr Val Ser Gly Phe Ser Leu
        35                  40                  45 gcc agc tat ggt gta gac tgg atc cgg cag ccc cca ggg aag gga ctg     192
Ala Ser Tyr Gly Val Asp Trp Ile Arg Gln Pro Pro Gly Lys Gly Leu
    50                  55                  60 gag tgg att ggg gta ata tgg ggt ggt gga agt aca aat tat aat tca     240
Glu Trp Ile Gly Val Ile Trp Gly Gly Gly Ser Thr Asn Tyr Asn Ser
65                  70                  75                  80 gct ctc atg tcc cga gtc acc ata tca gta gac acg tcc aag aac cag     288
Ala Leu Met Ser Arg Val Thr Ile Ser Val Asp Thr Ser Lys Asn Gln
                85                  90                  95 ttc tcc ctg aag ctg agc tct gtg acc gct gcg gac acg gcc gtg tat     336
Phe Ser Leu Lys Leu Ser Ser Val Thr Ala Ala Asp Thr Ala Val Tyr
            100                 105                 110 tac tgt gcg aga cat gga gat agt aat tcc ggt tat gct atg gac tac     384
Tyr Cys Ala Arg His Gly Asp Ser Asn Ser Gly Tyr Ala Met Asp Tyr
        115                 120                 125 tgg ggc caa ggt acc ctg gtc acc gtc tcg agt gct agc acc aag ggc     432
Trp Gly Gln Gly Thr Leu Val Thr Val Ser Ser Ala Ser Thr Lys Gly
    130                 135                 140 cca tcg gtc ttc ccc ctg gca ccc tcc tcc aag agc acc tct ggg ggc     480
Pro Ser Val Phe Pro Leu Ala Pro Ser Ser Lys Ser Thr Ser Gly Gly
145                 150                 155                 160 aca gcg gcc ctg ggc tgc ctg gtc aag gac tac ttc ccc gaa ccg gtg     528
Thr Ala Ala Leu Gly Cys Leu Val Lys Asp Tyr Phe Pro Glu Pro Val
                165                 170                 175
```

```
acg gtg tcg tgg aac tca ggc gcc ctg acc agc ggc gtg cac acc ttc     576
Thr Val Ser Trp Asn Ser Gly Ala Leu Thr Ser Gly Val His Thr Phe
            180                 185                 190 ccg gct gtc cta cag tcc tca gga ctc tac tcc ctc agc agc gtg gtg     624
Pro Ala Val Leu Gln Ser Ser Gly Leu Tyr Ser Leu Ser Ser Val Val
            195                 200                 205 acc gtg ccc tcc agc agc ttg ggc acc cag acc tac atc tgc aac gtg     672
Thr Val Pro Ser Ser Ser Leu Gly Thr Gln Thr Tyr Ile Cys Asn Val
    210                 215                 220 aat cac aag ccc agc aac acc aag gtg gac aag aga gtt gag ccc aaa     720
Asn His Lys Pro Ser Asn Thr Lys Val Asp Lys Arg Val Glu Pro Lys
225                 230                 235                 240 tct tgt gac aaa act cac aca tgc cca ccg tgc cca gca cct gaa ctc     768
Ser Cys Asp Lys Thr His Thr Cys Pro Pro Cys Pro Ala Pro Glu Leu
                245                 250                 255 ctg ggg gga ccg tca gtc ttc ctc ttc ccc cca aaa ccc aag gac acc     816
Leu Gly Gly Pro Ser Val Phe Leu Phe Pro Pro Lys Pro Lys Asp Thr
            260                 265                 270 ctc atg atc tcc cgg acc cct gag gtc aca tgc gtg gtg gtg gac gtg     864
Leu Met Ile Ser Arg Thr Pro Glu Val Thr Cys Val Val Val Asp Val
            275                 280                 285 agc cac gaa gac cct gag gtc aag ttc aac tgg tac gtg gac ggc gtg     912
Ser His Glu Asp Pro Glu Val Lys Phe Asn Trp Tyr Val Asp Gly Val
            290                 295                 300 gag gtg cat aat gcc aag aca aag ccg cgg gag gag cag tac aac agc     960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg    1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc    1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca    1104
Pro Ile Glu Lys Thr Ile Ser Lys Ala Lys Gly Gln Pro Arg Glu Pro
            355                 360                 365 cag gtg tac acc ctg ccc cca tcc cgg gat gag ctg acc aag aac cag    1152
Gln Val Tyr Thr Leu Pro Pro Ser Arg Asp Glu Leu Thr Lys Asn Gln
            370                 375                 380 gtc agc ctg acc tgc ctg gtc aaa ggc ttc tat ccc agc gac atc gcc    1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg    1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tac agc aag ctc    1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc    1344
Thr Val Asp Lys Ser Arg Trp Gln Gln Gly Asn Val Phe Ser Cys Ser
            435                 440                 445 gtg atg cat gag gct ctg cac aac cac tac acg cag aag agc ctc tcc    1392
Val Met His Glu Ala Leu His Asn His Tyr Thr Gln Lys Ser Leu Ser
    450                 455                 460 ctg tct ccg ggt aaa tga                                            1410
Leu Ser Pro Gly Lys
465
```

```
<210> SEQ ID NO 22
<211> LENGTH: 469
<212> TYPE: PRT
<213> ORGANISM: Artificial Sequence
<220> FEATURE:
<223> OTHER INFORMATION: Synthetic Construct

<400> SEQUENCE: 22

Met Ala Val Leu Val Leu Phe Leu Cys Leu Ala Phe Pro Ser Cys
1               5                   10                  15

Val Leu Thr Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Ala Ser Tyr Gly Val Asp Trp Ile Arg Gln Pro Pro Gly Lys Gly Leu
    50                  55                  60

Glu Trp Ile Gly Val Ile Trp Gly Gly Gly Ser Thr Asn Tyr Asn Ser
65                  70                  75                  80

Ala Leu Met Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg His Gly Asp Ser Asn Ser Gly Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365
```

```
Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 23
<211> LENGTH: 1410
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1410)
<223> OTHER INFORMATION: humanized heavy chain

<400> SEQUENCE: 23
```

| | | | | | | | | | | | | | | | | |
|---|---|---|---|---|---|---|---|---|---|---|---|---|---|---|---|---|
| atg | gct | gtc | ctg | gtg | ctg | ttc | ctc | tgc | ctg | gtt | gca | ttt | cca | agc | tgt | 48 |
| Met | Ala | Val | Leu | Val | Leu | Phe | Leu | Cys | Leu | Val | Ala | Phe | Pro | Ser | Cys | |
| 1 | | | | 5 | | | | | 10 | | | | | 15 | | |
| gtc | ctg | acc | cag | gtg | cag | ctg | cag | gag | tcg | ggc | cca | gga | ctg | gtg | aag | 96 |
| Val | Leu | Thr | Gln | Val | Gln | Leu | Gln | Glu | Ser | Gly | Pro | Gly | Leu | Val | Lys | |
| | | | 20 | | | | | 25 | | | | | 30 | | | |
| cct | tcg | gag | acc | ctg | tcc | ctc | acc | tgc | act | gtc | tct | ggg | ttt | tca | tta | 144 |
| Pro | Ser | Glu | Thr | Leu | Ser | Leu | Thr | Cys | Thr | Val | Ser | Gly | Phe | Ser | Leu | |
| | | | 35 | | | | | 40 | | | | | 45 | | | |
| gcc | agc | tat | ggt | gta | gac | tgg | atc | cgg | cag | ccc | cca | ggg | aag | gga | ctg | 192 |
| Ala | Ser | Tyr | Gly | Val | Asp | Trp | Ile | Arg | Gln | Pro | Pro | Gly | Lys | Gly | Leu | |
| | 50 | | | | | 55 | | | | | 60 | | | | | |
| gag | tgg | att | ggg | gta | ata | tgg | ggt | ggt | gga | agt | aca | aat | tat | aat | tca | 240 |
| Glu | Trp | Ile | Gly | Val | Ile | Trp | Gly | Gly | Gly | Ser | Thr | Asn | Tyr | Asn | Ser | |
| 65 | | | | | 70 | | | | | 75 | | | | | 80 | |
| tcc | ctc | atg | tcc | cga | gtc | acc | ata | tca | aaa | gac | acg | tcc | aag | aac | cag | 288 |
| Ser | Leu | Met | Ser | Arg | Val | Thr | Ile | Ser | Lys | Asp | Thr | Ser | Lys | Asn | Gln | |
| | | | | 85 | | | | | 90 | | | | | 95 | | |
| ctt | tcc | ctg | aag | ctg | agc | tct | gtg | acc | gct | gcg | gac | acg | gcc | gtg | tat | 336 |
| Leu | Ser | Leu | Lys | Leu | Ser | Ser | Val | Thr | Ala | Ala | Asp | Thr | Ala | Val | Tyr | |
| | | | | 100 | | | | | 105 | | | | | 110 | | |
| tac | tgt | gcg | aaa | cat | gga | gat | agt | aat | tcc | ggt | tat | gct | atg | gac | tac | 384 |
| Tyr | Cys | Ala | Lys | His | Gly | Asp | Ser | Asn | Ser | Gly | Tyr | Ala | Met | Asp | Tyr | |
| | | | | 115 | | | | | 120 | | | | | 125 | | |
| tgg | ggc | caa | ggt | acc | ctg | gtc | acc | gtc | tcg | agt | gct | agc | acc | aag | ggc | 432 |
| Trp | Gly | Gln | Gly | Thr | Leu | Val | Thr | Val | Ser | Ser | Ala | Ser | Thr | Lys | Gly | |
| | | 130 | | | | | 135 | | | | | 140 | | | | |
| cca | tcg | gtc | ttc | ccc | ctg | gca | ccc | tcc | tcc | aag | agc | acc | tct | ggg | ggc | 480 |
| Pro | Ser | Val | Phe | Pro | Leu | Ala | Pro | Ser | Ser | Lys | Ser | Thr | Ser | Gly | Gly | |
| 145 | | | | | 150 | | | | | 155 | | | | | 160 | |
| aca | gcg | gcc | ctg | ggc | tgc | ctg | gtc | aag | gac | tac | ttc | ccc | gaa | ccg | gtg | 528 |
| Thr | Ala | Ala | Leu | Gly | Cys | Leu | Val | Lys | Asp | Tyr | Phe | Pro | Glu | Pro | Val | |
| | | | | 165 | | | | | 170 | | | | | 175 | | |

```
acg gtg tcg tgg aac tca ggc gcc ctg acc agc ggc gtg cac acc ttc       576
Thr Val Ser Trp Asn Ser Gly Ala Leu Thr Ser Gly Val His Thr Phe
            180                 185                 190 ccg gct gtc cta cag tcc tca gga ctc tac tcc ctc agc agc gtg gtg       624
Pro Ala Val Leu Gln Ser Ser Gly Leu Tyr Ser Leu Ser Ser Val Val
        195                 200                 205 acc gtg ccc tcc agc agc ttg ggc acc cag acc tac atc tgc aac gtg       672
Thr Val Pro Ser Ser Ser Leu Gly Thr Gln Thr Tyr Ile Cys Asn Val
    210                 215                 220 aat cac aag ccc agc aac acc aag gtg gac aag aga gtt gag ccc aaa       720
Asn His Lys Pro Ser Asn Thr Lys Val Asp Lys Arg Val Glu Pro Lys
225                 230                 235                 240 tct tgt gac aaa act cac aca tgc cca ccg tgc cca gca cct gaa ctc       768
Ser Cys Asp Lys Thr His Thr Cys Pro Pro Cys Pro Ala Pro Glu Leu
                245                 250                 255 ctg ggg gga ccg tca gtc ttc ctc ttc ccc cca aaa ccc aag gac acc       816
Leu Gly Gly Pro Ser Val Phe Leu Phe Pro Pro Lys Pro Lys Asp Thr
            260                 265                 270 ctc atg atc tcc cgg acc cct gag gtc aca tgc gtg gtg gtg gac gtg       864
Leu Met Ile Ser Arg Thr Pro Glu Val Thr Cys Val Val Val Asp Val
        275                 280                 285 agc cac gaa gac cct gag gtc aag ttc aac tgg tac gtg gac ggc gtg       912
Ser His Glu Asp Pro Glu Val Lys Phe Asn Trp Tyr Val Asp Gly Val
    290                 295                 300 gag gtg cat aat gcc aag aca aag ccg cgg gag gag cag tac aac agc       960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg      1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc      1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca      1104
Pro Ile Glu Lys Thr Ile Ser Lys Ala Lys Gly Gln Pro Arg Glu Pro
        355                 360                 365 cag gtg tac acc ctg ccc cca tcc cgg gat gag ctg acc aag aac cag      1152
Gln Val Tyr Thr Leu Pro Pro Ser Arg Asp Glu Leu Thr Lys Asn Gln
    370                 375                 380 gtc agc ctg acc tgc ctg gtc aaa ggc ttc tat ccc agc gac atc gcc      1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg      1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tac agc aag ctc      1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc      1344
Thr Val Asp Lys Ser Arg Trp Gln Gln Gly Asn Val Phe Ser Cys Ser
        435                 440                 445 gtg atg cat gag gct ctg cac aac cac tac acg cag aag agc ctc tcc      1392
Val Met His Glu Ala Leu His Asn His Tyr Thr Gln Lys Ser Leu Ser
    450                 455                 460 ctg tct ccg ggt aaa tga                                              1410
Leu Ser Pro Gly Lys
465
```

```
<210> SEQ ID NO 24
<211> LENGTH: 469
<212> TYPE: PRT
<213> ORGANISM: Artificial Sequence
<220> FEATURE:
<223> OTHER INFORMATION: Synthetic Construct

<400> SEQUENCE: 24
```

Met Ala Val Leu Val Leu Phe Leu Cys Leu Ala Phe Pro Ser Cys
1               5                   10                  15

Val Leu Thr Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Ala Ser Tyr Gly Val Asp Trp Ile Arg Gln Pro Pro Gly Lys Gly Leu
    50                  55                  60

Glu Trp Ile Gly Val Ile Trp Gly Gly Ser Thr Asn Tyr Asn Ser
65                  70                  75                  80

Ser Leu Met Ser Arg Val Thr Ile Ser Lys Asp Thr Ser Lys Asn Gln
                85                  90                  95

Leu Ser Leu Lys Leu Ser Ser Val Thr Ala Ala Asp Thr Ala Val Tyr
            100                 105                 110

Tyr Cys Ala Lys His Gly Asp Ser Asn Ser Gly Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

```
Gln Val Tyr Thr Leu Pro Pro Ser Arg Asp Glu Leu Thr Lys Asn Gln
    370             375                 380

Val Ser Leu Thr Cys Leu Val Lys Gly Phe Tyr Pro Ser Asp Ile Ala
385             390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
    450                 455                 460

Leu Ser Pro Gly Lys
465

<210> SEQ ID NO 25
<211> LENGTH: 1410
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1410)
<223> OTHER INFORMATION: humanized heavy chain

<400> SEQUENCE: 25 atg gct gtc ctg gtg ctg ttc ctc tgc ctg gtt gca ttt cca agc tgt      48
Met Ala Val Leu Val Leu Phe Leu Cys Leu Val Ala Phe Pro Ser Cys
1               5                   10                  15 gtc ctg acc cag gtg cag ctg cag gag tcg ggc cca gga ctg gtg aag      96
Val Leu Thr Gln Val Gln Leu Gln Glu Ser Gly Pro Gly Leu Val Lys
            20                  25                  30 cct tcg gag acc ctg tcc ctc acc tgc act gtc tct ggg ttt tca tta     144
Pro Ser Glu Thr Leu Ser Leu Thr Cys Thr Val Ser Gly Phe Ser Leu
        35                  40                  45 gcc agc tat ggt gta gac tgg gtt cgg cag ccc cca ggg aag gga ctg     192
Ala Ser Tyr Gly Val Asp Trp Val Arg Gln Pro Pro Gly Lys Gly Leu
    50                  55                  60 gag tgg att ggg gta ata tgg ggt ggt gga agt aca aat tat aat tca     240
Glu Trp Ile Gly Val Ile Trp Gly Gly Gly Ser Thr Asn Tyr Asn Ser
65                  70                  75                  80 gct ctc atg tcc cga ctt acc ata tca aaa gac aac tcc aag agc cag     288
Ala Leu Met Ser Arg Leu Thr Ile Ser Lys Asp Asn Ser Lys Ser Gln
                85                  90                  95 ctt tcc ctg aag ctg agc tct gtg acc gct gcg gac acg gcc gtg tat     336
Leu Ser Leu Lys Leu Ser Ser Val Thr Ala Ala Asp Thr Ala Val Tyr
            100                 105                 110 tac tgt gcg aaa cat gga gat agt aat tcc ggt tat gct atg gac tac     384
Tyr Cys Ala Lys His Gly Asp Ser Asn Ser Gly Tyr Ala Met Asp Tyr
        115                 120                 125 tgg ggc caa ggt acc ctg gtc acc gtc tcg agt gct agc acc aag ggc     432
Trp Gly Gln Gly Thr Leu Val Thr Val Ser Ser Ala Ser Thr Lys Gly
    130                 135                 140 cca tcg gtc ttc ccc ctg gca ccc tcc tcc aag agc acc tct ggg ggc     480
Pro Ser Val Phe Pro Leu Ala Pro Ser Ser Lys Ser Thr Ser Gly Gly
145                 150                 155                 160 aca gcg gcc ctg ggc tgc ctg gtc aag gac tac ttc ccc gaa ccg gtg     528
Thr Ala Ala Leu Gly Cys Leu Val Lys Asp Tyr Phe Pro Glu Pro Val
                165                 170                 175
```

```
acg gtg tcg tgg aac tca ggc gcc ctg acc agc ggc gtg cac acc ttc      576
Thr Val Ser Trp Asn Ser Gly Ala Leu Thr Ser Gly Val His Thr Phe
            180                 185                 190 ccg gct gtc cta cag tcc tca gga ctc tac tcc ctc agc agc gtg gtg      624
Pro Ala Val Leu Gln Ser Ser Gly Leu Tyr Ser Leu Ser Ser Val Val
        195                 200                 205 acc gtg ccc tcc agc agc ttg ggc acc cag acc tac atc tgc aac gtg      672
Thr Val Pro Ser Ser Ser Leu Gly Thr Gln Thr Tyr Ile Cys Asn Val
    210                 215                 220 aat cac aag ccc agc aac acc aag gtg gac aag aga gtt gag ccc aaa      720
Asn His Lys Pro Ser Asn Thr Lys Val Asp Lys Arg Val Glu Pro Lys
225                 230                 235                 240 tct tgt gac aaa act cac aca tgc cca ccg tgc cca gca cct gaa ctc      768
Ser Cys Asp Lys Thr His Thr Cys Pro Pro Cys Pro Ala Pro Glu Leu
                245                 250                 255 ctg ggg gga ccg tca gtc ttc ctc ttc ccc cca aaa ccc aag gac acc      816
Leu Gly Gly Pro Ser Val Phe Leu Phe Pro Pro Lys Pro Lys Asp Thr
            260                 265                 270 ctc atg atc tcc cgg acc cct gag gtc aca tgc gtg gtg gtg gac gtg      864
Leu Met Ile Ser Arg Thr Pro Glu Val Thr Cys Val Val Val Asp Val
        275                 280                 285 agc cac gaa gac cct gag gtc aag ttc aac tgg tac gtg gac ggc gtg      912
Ser His Glu Asp Pro Glu Val Lys Phe Asn Trp Tyr Val Asp Gly Val
    290                 295                 300 gag gtg cat aat gcc aag aca aag ccg cgg gag gag cag tac aac agc      960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg     1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc     1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca     1104
Pro Ile Glu Lys Thr Ile Ser Lys Ala Lys Gly Gln Pro Arg Glu Pro
        355                 360                 365 cag gtg tac acc ctg ccc cca tcc cgg gat gag ctg acc aag aac cag     1152
Gln Val Tyr Thr Leu Pro Pro Ser Arg Asp Glu Leu Thr Lys Asn Gln
    370                 375                 380 gtc agc ctg acc tgc ctg gtc aaa ggc ttc tat ccc agc gac atc gcc     1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg     1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tac agc aag ctc     1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc     1344
Thr Val Asp Lys Ser Arg Trp Gln Gln Gly Asn Val Phe Ser Cys Ser
        435                 440                 445 gtg atg cat gag gct ctg cac aac cac tac acg cag aag agc ctc tcc     1392
Val Met His Glu Ala Leu His Asn His Tyr Thr Gln Lys Ser Leu Ser
    450                 455                 460 ctg tct ccg ggt aaa tga                                              1410
Leu Ser Pro Gly Lys
465
```

-continued

```
<210> SEQ ID NO 26
<211> LENGTH: 469
<212> TYPE: PRT
<213> ORGANISM: Artificial Sequence
<220> FEATURE:
<223> OTHER INFORMATION: Synthetic Construct

<400> SEQUENCE: 26

Met Ala Val Leu Val Leu Phe Leu Cys Leu Ala Phe Pro Ser Cys
1               5                   10                  15

Val Leu Thr Gln Val Gln Leu Gln Glu Ser Gly Pro Gly Leu Val Lys
                20                  25                  30

Pro Ser Glu Thr Leu Ser Leu Thr Cys Thr Val Ser Gly Phe Ser Leu
            35                  40                  45

Ala Ser Tyr Gly Val Asp Trp Val Arg Gln Pro Pro Gly Lys Gly Leu
        50                  55                  60

Glu Trp Ile Gly Val Ile Trp Gly Gly Gly Ser Thr Asn Tyr Asn Ser
65                  70                  75                  80

Ala Leu Met Ser Arg Leu Thr Ile Ser Lys Asp Asn Ser Lys Ser Gln
                85                  90                  95

Leu Ser Leu Lys Leu Ser Ser Val Thr Ala Ala Asp Thr Ala Val Tyr
            100                 105                 110

Tyr Cys Ala Lys His Gly Asp Ser Asn Ser Gly Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365
```

```
Gln Val Tyr Thr Leu Pro Pro Ser Arg Asp Glu Leu Thr Lys Asn Gln
    370             375                 380

Val Ser Leu Thr Cys Leu Val Lys Gly Phe Tyr Pro Ser Asp Ile Ala
385             390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450             455                 460

Leu Ser Pro Gly Lys
465

<210> SEQ ID NO 27
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(708)
<223> OTHER INFORMATION: humanized light chain

<400> SEQUENCE: 27 atg gat ttt caa gtg cag att ttc agc ttc ctg cta atc agt gcc tca        48
Met Asp Phe Gln Val Gln Ile Phe Ser Phe Leu Leu Ile Ser Ala Ser
1               5                   10                  15 gtc ata atg tcc aga gga gaa att gtg ttg aca cag tct cca gcc acc        96
Val Ile Met Ser Arg Gly Glu Ile Val Leu Thr Gln Ser Pro Ala Thr
            20                  25                  30 ctg tct ttg tct cca ggg gaa aga gcc acc ctc tcc tgc agt gcc agc       144
Leu Ser Leu Ser Pro Gly Glu Arg Ala Thr Leu Ser Cys Ser Ala Ser
        35                  40                  45 cca agt gta agt tac atg cac tgg tac caa cag aaa cct ggc cag gct       192
Pro Ser Val Ser Tyr Met His Trp Tyr Gln Gln Lys Pro Gly Gln Ala
    50                  55                  60 ccc agg ctc ctc atc tat gac aca tac aaa ctg gct tct ggc atc cca       240
Pro Arg Leu Leu Ile Tyr Asp Thr Tyr Lys Leu Ala Ser Gly Ile Pro
65                  70                  75                  80 gcc agg ttc agt ggc agt ggg tct ggg aca gac ttc act ctc acc atc       288
Ala Arg Phe Ser Gly Ser Gly Ser Gly Thr Asp Phe Thr Leu Thr Ile
                85                  90                  95 agc agc cta gag cct gaa gat ttt gca gtt tat tac tgt ttt cag ggg       336
Ser Ser Leu Glu Pro Glu Asp Phe Ala Val Tyr Tyr Cys Phe Gln Gly
            100                 105                 110 agt ggg ttc cca ctc acg ttt ggc cag ggg acc aag gtg gaa atc aaa       384
Ser Gly Phe Pro Leu Thr Phe Gly Gln Gly Thr Lys Val Glu Ile Lys
        115                 120                 125 cgt acg gtg gct gca cca tct gtc ttc atc ttc ccg cca tct gat gag       432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc       480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa       528
Tyr Pro Arg Glu Ala Lys Val Gln Trp Lys Val Asp Asn Ala Leu Gln
                165                 170                 175
```

```
tcg ggt aac tcc cag gag agt gtc aca gag cag gac agc aag gac agc      576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag      624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg      672
Lys His Lys Val Tyr Ala Cys Glu Val Thr His Gln Gly Leu Ser Ser
    210                 215                 220 ccc gtc aca aag agc ttc aac agg gga gag tgt tag                       708
Pro Val Thr Lys Ser Phe Asn Arg Gly Glu Cys
225                 230                 235
```

<210> SEQ ID NO 28
<211> LENGTH: 235
<212> TYPE: PRT
<213> ORGANISM: Artificial Sequence
<220> FEATURE:
<223> OTHER INFORMATION: Synthetic Construct

<400> SEQUENCE: 28

```
Met Asp Phe Gln Val Gln Ile Phe Ser Phe Leu Leu Ile Ser Ala Ser
1               5                   10                  15

Val Ile Met Ser Arg Gly Glu Ile Val Leu Thr Gln Ser Pro Ala Thr
            20                  25                  30

Leu Ser Leu Ser Pro Gly Glu Arg Ala Thr Leu Ser Cys Ser Ala Ser
        35                  40                  45

Pro Ser Val Ser Tyr Met His Trp Tyr Gln Gln Lys Pro Gly Gln Ala
    50                  55                  60

Pro Arg Leu Leu Ile Tyr Asp Thr Tyr Lys Leu Ala Ser Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Phe Gln Gly
            100                 105                 110

Ser Gly Phe Pro Leu Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 29
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(708)
<223> OTHER INFORMATION: humanized light chain

<400> SEQUENCE: 29

| | | | | | | | | | | | | | | | | |
|---|---|---|---|---|---|---|---|---|---|---|---|---|---|---|---|---|
| atg | gat | ttt | caa | gtg | cag | att | ttc | agc | ttc | ctg | cta | atc | agt | gcc | tca | 48 |
| Met | Asp | Phe | Gln | Val | Gln | Ile | Phe | Ser | Phe | Leu | Leu | Ile | Ser | Ala | Ser | |
| 1 | | | | 5 | | | | | 10 | | | | | 15 | | |
| gtc | ata | atg | tcc | aga | gga | gaa | aat | gtg | ttg | aca | cag | tct | cca | gcc | acc | 96 |
| Val | Ile | Met | Ser | Arg | Gly | Glu | Asn | Val | Leu | Thr | Gln | Ser | Pro | Ala | Thr | |
| | | | 20 | | | | | 25 | | | | | 30 | | | |
| ctg | tct | ttg | tct | cca | ggg | gaa | aga | gcc | acc | ctc | tcc | tgc | agt | gcc | agc | 144 |
| Leu | Ser | Leu | Ser | Pro | Gly | Glu | Arg | Ala | Thr | Leu | Ser | Cys | Ser | Ala | Ser | |
| | | 35 | | | | | 40 | | | | | 45 | | | | |
| cca | agt | gta | agt | tac | atg | cac | tgg | tac | caa | cag | aaa | cct | ggc | cag | gct | 192 |
| Pro | Ser | Val | Ser | Tyr | Met | His | Trp | Tyr | Gln | Gln | Lys | Pro | Gly | Gln | Ala | |
| 50 | | | | | 55 | | | | | 60 | | | | | | |
| ccc | agg | ctc | ctc | atc | tat | gac | aca | tac | aaa | ctg | gct | tct | ggc | atc | cca | 240 |
| Pro | Arg | Leu | Leu | Ile | Tyr | Asp | Thr | Tyr | Lys | Leu | Ala | Ser | Gly | Ile | Pro | |
| 65 | | | | | 70 | | | | | 75 | | | | | 80 | |
| gcc | agg | ttc | agt | ggc | agt | ggg | tct | ggg | aac | gac | tac | act | ctc | acc | atc | 288 |
| Ala | Arg | Phe | Ser | Gly | Ser | Gly | Ser | Gly | Asn | Asp | Tyr | Thr | Leu | Thr | Ile | |
| | | | | 85 | | | | | 90 | | | | | 95 | | |
| agc | agc | cta | gag | cct | gaa | gat | ttt | gca | gtt | tat | tac | tgt | ttt | cag | ggg | 336 |
| Ser | Ser | Leu | Glu | Pro | Glu | Asp | Phe | Ala | Val | Tyr | Tyr | Cys | Phe | Gln | Gly | |
| | | | 100 | | | | | 105 | | | | | 110 | | | |
| agt | ggg | ttc | cca | ctc | acg | ttt | ggc | cag | ggg | acc | aag | gtg | gaa | atc | aaa | 384 |
| Ser | Gly | Phe | Pro | Leu | Thr | Phe | Gly | Gln | Gly | Thr | Lys | Val | Glu | Ile | Lys | |
| | | 115 | | | | | 120 | | | | | 125 | | | | |
| cgt | acg | gtg | gct | gca | cca | tct | gtc | ttc | atc | ttc | ccg | cca | tct | gat | gag | 432 |
| Arg | Thr | Val | Ala | Ala | Pro | Ser | Val | Phe | Ile | Phe | Pro | Pro | Ser | Asp | Glu | |
| 130 | | | | | 135 | | | | | 140 | | | | | | |
| cag | ttg | aaa | tct | gga | act | gcc | tct | gtt | gtg | tgc | ctg | ctg | aat | aac | ttc | 480 |
| Gln | Leu | Lys | Ser | Gly | Thr | Ala | Ser | Val | Val | Cys | Leu | Leu | Asn | Asn | Phe | |
| 145 | | | | | 150 | | | | | 155 | | | | | 160 | |
| tat | ccc | aga | gag | gcc | aaa | gta | cag | tgg | aag | gtg | gat | aac | gcc | ctc | caa | 528 |
| Tyr | Pro | Arg | Glu | Ala | Lys | Val | Gln | Trp | Lys | Val | Asp | Asn | Ala | Leu | Gln | |
| | | | | 165 | | | | | 170 | | | | | 175 | | |
| tcg | ggt | aac | tcc | cag | gag | agt | gtc | aca | gag | cag | gac | agc | aag | gac | agc | 576 |
| Ser | Gly | Asn | Ser | Gln | Glu | Ser | Val | Thr | Glu | Gln | Asp | Ser | Lys | Asp | Ser | |
| | | | 180 | | | | | 185 | | | | | 190 | | | |
| acc | tac | agc | ctc | agc | agc | acc | ctg | acg | ctg | agc | aaa | gca | gac | tac | gag | 624 |
| Thr | Tyr | Ser | Leu | Ser | Ser | Thr | Leu | Thr | Leu | Ser | Lys | Ala | Asp | Tyr | Glu | |
| | | 195 | | | | | 200 | | | | | 205 | | | | |
| aaa | cac | aaa | gtc | tac | gcc | tgc | gaa | gtc | acc | cat | cag | ggc | ctg | agc | tcg | 672 |
| Lys | His | Lys | Val | Tyr | Ala | Cys | Glu | Val | Thr | His | Gln | Gly | Leu | Ser | Ser | |
| 210 | | | | | 215 | | | | | 220 | | | | | | |
| ccc | gtc | aca | aag | agc | ttc | aac | agg | gga | gag | tgt | tag | | | | | 708 |
| Pro | Val | Thr | Lys | Ser | Phe | Asn | Arg | Gly | Glu | Cys | | | | | | |
| 225 | | | | | 230 | | | | | 235 | | | | | | |

<210> SEQ ID NO 30
<211> LENGTH: 235
<212> TYPE: PRT
<213> ORGANISM: Artificial Sequence
<220> FEATURE:
<223> OTHER INFORMATION: Synthetic Construct

<400> SEQUENCE: 30

Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Thr
            20                  25                  30

Leu Ser Leu Ser Pro Gly Glu Arg Ala Thr Leu Ser Cys Ser Ala Ser
        35                  40                  45

Pro Ser Val Ser Tyr Met His Trp Tyr Gln Gln Lys Pro Gly Gln Ala
    50                  55                  60

Pro Arg Leu Leu Ile Tyr Asp Thr Tyr Lys Leu Ala Ser Gly Ile Pro
65                  70                  75                  80

Ala Arg Phe Ser Gly Ser Gly Ser Gly Asn Asp Tyr Thr Leu Thr Ile
                85                  90                  95

Ser Ser Leu Glu Pro Glu Asp Phe Ala Val Tyr Tyr Cys Phe Gln Gly
            100                 105                 110

Ser Gly Phe Pro Leu Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 31
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(708)
<223> OTHER INFORMATION: humanized light chain

<400> SEQUENCE: 31 atg gat ttt caa gtg cag att ttc agc ttc ctg cta atc agt gcc tca    48
Met Asp Phe Gln Val Gln Ile Phe Ser Phe Leu Leu Ile Ser Ala Ser
1               5                   10                  15 gtc ata atg tcc aga gga gaa aat gtg ttg aca cag tct cca gcc acc    96
Val Ile Met Ser Arg Gly Glu Asn Val Leu Thr Gln Ser Pro Ala Thr
            20                  25                  30 ctg tct ttg tct cca ggg gaa aga gcc acc ctc tcc tgc agt gcc agc    144
Leu Ser Leu Ser Pro Gly Glu Arg Ala Thr Leu Ser Cys Ser Ala Ser
        35                  40                  45 cca agt gta agt tac atg cac tgg tac caa cag aaa cct ggc cag gct    192
Pro Ser Val Ser Tyr Met His Trp Tyr Gln Gln Lys Pro Gly Gln Ala
    50                  55                  60

```
ccc agg ctc tgg atc tat gac aca tac aaa ctg gct tct ggc atc cca    240
Pro Arg Leu Trp Ile Tyr Asp Thr Tyr Lys Leu Ala Ser Gly Ile Pro
 65                  70                  75                  80 gcc agg ttc agt ggc agt ggg tct ggg aac gac tac act ctc acc atc    288
Ala Arg Phe Ser Gly Ser Gly Ser Gly Asn Asp Tyr Thr Leu Thr Ile
             85                  90                  95 agc agc cta gag cct gaa gat ttt gca gtt tat tac tgt ttt cag ggg    336
Ser Ser Leu Glu Pro Glu Asp Phe Ala Val Tyr Tyr Cys Phe Gln Gly
            100                 105                 110 agt ggg ttc cca ctc acg ttt ggc cag ggg acc aag gtg gaa atc aaa    384
Ser Gly Phe Pro Leu Thr Phe Gly Gln Gly Thr Lys Val Glu Ile Lys
        115                 120                 125 cgt acg gtg gct gca cca tct gtc ttc atc ttc ccg cca tct gat gag    432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc    480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa    528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc    576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag    624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg    672
Lys His Lys Val Tyr Ala Cys Glu Val Thr His Gln Gly Leu Ser Ser
    210                 215                 220 ccc gtc aca aag agc ttc aac agg gga gag tgt tag                    708
Pro Val Thr Lys Ser Phe Asn Arg Gly Glu Cys
225                 230                 235

<210> SEQ ID NO 32
<211> LENGTH: 235
<212> TYPE: PRT
<213> ORGANISM: Artificial Sequence
<220> FEATURE:
<223> OTHER INFORMATION: Synthetic Construct

<400> SEQUENCE: 32

Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Thr
            20                  25                  30

Leu Ser Leu Ser Pro Gly Glu Arg Ala Thr Leu Ser Cys Ser Ala Ser
        35                  40                  45

Pro Ser Val Ser Tyr Met His Trp Tyr Gln Gln Lys Pro Gly Gln Ala
    50                  55                  60

Pro Arg Leu Trp Ile Tyr Asp Thr Tyr Lys Leu Ala Ser Gly Ile Pro
65                  70                  75                  80

Ala Arg Phe Ser Gly Ser Gly Ser Gly Asn Asp Tyr Thr Leu Thr Ile
            85                  90                  95

Ser Ser Leu Glu Pro Glu Asp Phe Ala Val Tyr Tyr Cys Phe Gln Gly
        100                 105                 110

Ser Gly Phe Pro Leu Thr Phe Gly Gln Gly Thr Lys Val Glu Ile Lys
    115                 120                 125
```

-continued

```
Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 33
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: H-CDR1

<400> SEQUENCE: 33

Gly Phe Ser Leu Thr Ser Tyr Gly Val Asp
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: H-CDR2

<400> SEQUENCE: 34

Val Ile Trp Gly Gly Gly Ser Thr Asn Tyr Asn Ser Ala Leu Met Ser
1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: H-CDR3

<400> SEQUENCE: 35

His Glu Val Leu Arg Gly Tyr Ala Leu Asp Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: L-CDR1
```

```
<400> SEQUENCE: 36

Ser Ala Ser Ser Ser Val Ser Tyr Met His
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: L-CDR2

<400> SEQUENCE: 37

Asp Thr Ser Lys Leu Ala Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: L-CDR3

<400> SEQUENCE: 38

Phe Gln Gly Ser Gly Tyr Pro Leu Thr
1               5

<210> SEQ ID NO 39
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: H-CDR2

<400> SEQUENCE: 39

Val Ile Trp Gly Gly Gly Ser Thr Asn Tyr Asn Ser Ser Leu Met Ser
1               5                   10                  15

<210> SEQ ID NO 40
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: H-CDR1

<400> SEQUENCE: 40

Gly Phe Ser Leu Ala Ser Tyr Gly Val Asp
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: H-CDR3
```

<400> SEQUENCE: 41

His Gly Asp Ser Asn Ser Gly Tyr Ala Met Asp Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: L-CDR1

<400> SEQUENCE: 42

Ser Ala Ser Pro Ser Val Ser Tyr Met His
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: L-CDR2

<400> SEQUENCE: 43

Asp Thr Tyr Lys Leu Ala Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: L-CDR3

<400> SEQUENCE: 44

Phe Gln Gly Ser Gly Phe Pro Leu Thr
1               5

<210> SEQ ID NO 45
<211> LENGTH: 21
<212> TYPE: DNA
<213> ORGANISM: Artificial Sequence
<220> FEATURE:
<223> OTHER INFORMATION: Synthetic primer

<400> SEQUENCE: 45
tatgcaaggc ttacaaccac a                                        21

<210> SEQ ID NO 46
<211> LENGTH: 21
<212> TYPE: DNA
<213> ORGANISM: Artificial Sequence
<220> FEATURE:
<223> OTHER INFORMATION: Synthetic primer

<400> SEQUENCE: 46
gggggtactg ggcttgggta t                                        21

```
<210> SEQ ID NO 47
<211> LENGTH: 24
<212> TYPE: DNA
<213> ORGANISM: Artificial Sequence
<220> FEATURE:
<223> OTHER INFORMATION: Synthetic primer

<400> SEQUENCE: 47
ctcattcctg ttgaagctct tgac                                          24

<210> SEQ ID NO 48
<211> LENGTH: 37
<212> TYPE: DNA
<213> ORGANISM: Artificial Sequence
<220> FEATURE:
<223> OTHER INFORMATION: Synthetic primer

<400> SEQUENCE: 48
gtgactcgag tcgacatcga tttttttttt tttttt                             37

<210> SEQ ID NO 49
<211> LENGTH: 38
<212> TYPE: DNA
<213> ORGANISM: Artificial Sequence
<220> FEATURE:
<223> OTHER INFORMATION: Synthetic primer

<400> SEQUENCE: 49
cttccggaat tcctcaattt tcttgtccac cttggtgc                           38

<210> SEQ ID NO 50
<211> LENGTH: 38
<212> TYPE: DNA
<213> ORGANISM: Artificial Sequence
<220> FEATURE:
<223> OTHER INFORMATION: Synthetic primer

<400> SEQUENCE: 50
cttccggaat tcctcgattc tcttgatcaa ctcagtct                           38

<210> SEQ ID NO 51
<211> LENGTH: 42
<212> TYPE: DNA
<213> ORGANISM: Artificial Sequence
<220> FEATURE:
<223> OTHER INFORMATION: Synthetic primer

<400> SEQUENCE: 51
cttccggaat tcctcattcc tgttgaagct cttgacaatg gg                      42

<210> SEQ ID NO 52
<211> LENGTH: 38
<212> TYPE: DNA
<213> ORGANISM: Artificial Sequence
<220> FEATURE:
<223> OTHER INFORMATION: Synthetic primer

<400> SEQUENCE: 52
attaagtcga catagacaga tgggggtgtc gttttggc                           38

<210> SEQ ID NO 53
<211> LENGTH: 35
<212> TYPE: DNA
<213> ORGANISM: Artificial Sequence
<220> FEATURE:
<223> OTHER INFORMATION: Synthetic primer
```

<400> SEQUENCE: 53
attaagtcga cagggaccaa gggatagaca gatgg                                35

<210> SEQ ID NO 54
<211> LENGTH: 31
<212> TYPE: DNA
<213> ORGANISM: Artificial Sequence
<220> FEATURE:
<223> OTHER INFORMATION: Synthetic primer

<400> SEQUENCE: 54
ctacctcgag ggatacagtt ggtgcagcat c                                   31

<210> SEQ ID NO 55
<211> LENGTH: 39
<212> TYPE: DNA
<213> ORGANISM: Artificial Sequence
<220> FEATURE:
<223> OTHER INFORMATION: Synthetic primer

<400> SEQUENCE: 55
cagtccgcgg ccaccatgga ttttcaagtg cagattttc                           39

<210> SEQ ID NO 56
<211> LENGTH: 31
<212> TYPE: DNA
<213> ORGANISM: Artificial Sequence
<220> FEATURE:
<223> OTHER INFORMATION: Synthetic primer

<400> SEQUENCE: 56
aggaagatct aacactcatt cctgttgaag c                                   31

<210> SEQ ID NO 57
<211> LENGTH: 35
<212> TYPE: DNA
<213> ORGANISM: Artificial Sequence
<220> FEATURE:
<223> OTHER INFORMATION: Synthetic primer

<400> SEQUENCE: 57
cagtccgcgg ccaccatggc tgtcctggtg ctgtt                               35

<210> SEQ ID NO 58
<211> LENGTH: 23
<212> TYPE: DNA
<213> ORGANISM: Artificial Sequence
<220> FEATURE:
<223> OTHER INFORMATION: Synthetic primer

<400> SEQUENCE: 58
ctggacaggg atccagagtt cca                                            23

<210> SEQ ID NO 59
<211> LENGTH: 30
<212> TYPE: DNA
<213> ORGANISM: Artificial Sequence
<220> FEATURE:
<223> OTHER INFORMATION: Synthetic primer

<400> SEQUENCE: 59
catgagatct catttaccag gggagcgaga                                     30

```
<210> SEQ ID NO 60
<211> LENGTH: 108
<212> TYPE: PRT
<213> ORGANISM: Homo sapiens
<220> FEATURE:
<221> NAME/KEY: misc_feature
<223> OTHER INFORMATION: huIGHV4-59x01

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gln Gly Thr Leu Val Thr Val Ser Ser
            100                 105

<210> SEQ ID NO 61
<211> LENGTH: 105
<212> TYPE: PRT
<213> ORGANISM: Homo sapiens
<220> FEATURE:
<221> NAME/KEY: misc_feature
<223> OTHER INFORMATION: huIGKV3-11x01

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Gly Gln Gly Thr Lys Val Glu Ile Lys
            100                 105
```